US012661224B2

(12) United States Patent
Conklin et al.

(10) Patent No.: US 12,661,224 B2
(45) Date of Patent: Jun. 23, 2026

(54) PROSTHETIC VALVE HOLDERS WITH AUTOMATIC DEPLOYING MECHANISMS

(71) Applicant: Edwards Lifesciences Corporation, Irvine, CA (US)

(72) Inventors: Brian S. Conklin, Orange, CA (US); Michael C. Murad, Lake Mathews, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1029 days.

(21) Appl. No.: 17/810,206

(22) Filed: Jun. 30, 2022

(65) Prior Publication Data

US 2022/0331100 A1 Oct. 20, 2022

Related U.S. Application Data

(60) Continuation of application No. 16/673,487, filed on Nov. 4, 2019, now Pat. No. 11,376,125, which is a division of application No. 15/481,283, filed on Apr. 6, 2017, now Pat. No. 10,463,485.

(51) Int. Cl.
*A61F 2/24* (2006.01)
(52) U.S. Cl.
CPC .... *A61F 2/2427* (2013.01); *A61F 2220/0091* (2013.01)
(58) Field of Classification Search
CPC .......... A61F 2/24; A61F 2/2427; A61F 2/243; A61F 2/2472
See application file for complete search history.

(56) References Cited

U.S. PATENT DOCUMENTS

| | | | |
|---|---|---|---|
| 3,143,742 | A | 8/1964 | Cromie |
| 3,320,972 | A | 5/1967 | High et al. |
| 3,371,352 | A | 3/1968 | Siposs et al. |
| 3,546,710 | A | 12/1970 | Shumakov et al. |
| 3,574,865 | A | 4/1971 | Hamaker |
| 3,755,823 | A | 9/1973 | Hancock |
| 3,839,741 | A | 10/1974 | Haller |

(Continued)

FOREIGN PATENT DOCUMENTS

| | | |
|---|---|---|
| EP | 0125393 A1 | 11/1984 |
| EP | 0143246 A2 | 6/1985 |

(Continued)

*Primary Examiner* — Christopher D. Prone
(74) *Attorney, Agent, or Firm* — Guy Cumberbatch

(57) ABSTRACT

A valve holder for delivering a prosthetic heart valve to an implant site is in various embodiments configured to reduce or eliminate the occurrence of suture looping or other damage to the prosthetic valve during implantation. The valve holder can be configured to deploy or actuate automatically when performing preparatory steps that are already familiar to practitioners, such as attaching a delivery handle to the valve holder, so that the valve holders will not require additional steps or training to use. Therefore, operation of the valve holders is kept simple, and occurrences of mistakes caused by user error can be minimized or reduced. Valve holders according to different embodiments can be designed to accommodate implantation of prosthetic heart valves from either the inflow end or the outflow end of the native valve annulus.

20 Claims, 15 Drawing Sheets

(56) References Cited

U.S. PATENT DOCUMENTS

| | | | |
|---|---|---|---|
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,501,030 A | 2/1985 | Lane |
| 4,506,394 A | 3/1985 | Bedard |
| 4,535,483 A | 8/1985 | Klawitter et al. |
| 4,566,465 A | 1/1986 | Arhan et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,955 A | 11/1992 | Love et al. |
| 5,258,023 A | 11/1993 | Reger |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,014 A | 11/1994 | Sauter et al. |
| 5,360,444 A | 11/1994 | Kusuhara |
| 5,376,112 A | 12/1994 | Duran |
| 5,396,887 A | 3/1995 | Imran |
| 5,397,351 A | 3/1995 | Pavcnik et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,487,760 A | 1/1996 | Villafana |
| 5,488,789 A | 2/1996 | Religa et al. |
| 5,489,296 A | 2/1996 | Love et al. |
| 5,489,297 A | 2/1996 | Duran |
| 5,489,298 A | 2/1996 | Love et al. |
| 5,500,016 A | 3/1996 | Fisher |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,697,382 A | 12/1997 | Love et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,800,527 A | 9/1998 | Jansen et al. |
| 5,814,097 A | 9/1998 | Sterman et al. |
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,855,801 A | 1/1999 | Lin et al. |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,554 A | 3/2000 | Rosenman et al. |
| 6,042,607 A | 3/2000 | Williamson, IV et al. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,283,127 B1 | 9/2001 | Sterman et al. |
| 6,287,339 B1 | 9/2001 | Vazquez et al. |
| 6,290,674 B1 | 9/2001 | Roue et al. |
| 6,312,447 B1 | 11/2001 | Grimes |
| 6,312,465 B1 | 11/2001 | Griffin et al. |
| 6,328,727 B1 | 12/2001 | Frazier et al. |
| 6,350,282 B1 | 2/2002 | Eberhardt |
| 6,371,983 B1 | 4/2002 | Lane |
| 6,375,620 B1 | 4/2002 | Oser et al. |
| 6,402,780 B2 | 6/2002 | Williamson, IV et al. |
| 6,409,674 B1 | 6/2002 | Brockway et al. |
| 6,425,916 B1 | 7/2002 | Garrison et al. |
| 6,440,164 B1 | 8/2002 | DiMatteo et al. |
| 6,442,413 B1 | 8/2002 | Silver |
| 6,454,799 B1 | 9/2002 | Schreck |
| 6,458,153 B1 | 10/2002 | Bailey et al. |
| 6,468,305 B1 | 10/2002 | Otte |
| 6,491,624 B1 | 12/2002 | Lotfi |
| 6,582,462 B1 | 6/2003 | Andersen et al. |
| 6,585,766 B1 | 7/2003 | Huynh et al. |
| 6,645,143 B2 | 11/2003 | VanTassel et al. |
| 6,652,464 B2 | 11/2003 | Schwartz et al. |
| 6,652,578 B2 | 11/2003 | Bailey et al. |
| 6,675,049 B2 | 1/2004 | Thompson et al. |
| 6,682,559 B2 | 1/2004 | Myers et al. |
| 6,685,739 B2 | 2/2004 | DiMatteo et al. |

(56) References Cited

U.S. PATENT DOCUMENTS

| | | |
|---|---|---|
| 6,730,118 B2 | 5/2004 | Spenser et al. |
| 6,733,525 B2 | 5/2004 | Yang et al. |
| 6,741,885 B1 | 5/2004 | Park et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,795,732 B2 | 9/2004 | Stadler et al. |
| 6,805,711 B2 | 10/2004 | Quijano et al. |
| 6,893,459 B1 | 5/2005 | Macoviak |
| 6,893,460 B2 | 5/2005 | Spenser et al. |
| 6,895,265 B2 | 5/2005 | Silver |
| 6,908,481 B2 | 6/2005 | Cribier |
| 6,939,365 B1 | 9/2005 | Fogarty et al. |
| 6,966,925 B2 | 11/2005 | Stobie |
| 7,011,681 B2 | 3/2006 | Vesely |
| 7,018,404 B2 | 3/2006 | Holmberg et al. |
| 7,025,780 B2 | 4/2006 | Gabbay |
| 7,033,322 B2 | 4/2006 | Silver |
| 7,052,466 B2 | 5/2006 | Scheiner et al. |
| 7,070,616 B2 | 7/2006 | Majercak et al. |
| 7,082,330 B2 | 7/2006 | Stadler et al. |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| RE40,377 E | 6/2008 | Williamson, IV et al. |
| 7,416,530 B2 | 8/2008 | Turner et al. |
| 7,422,603 B2 | 9/2008 | Lane |
| 7,513,909 B2 | 4/2009 | Lane et al. |
| 7,556,647 B2 | 7/2009 | Drews et al. |
| 7,569,072 B2 | 8/2009 | Berg et al. |
| 7,621,878 B2 | 11/2009 | Ericson et al. |
| 7,916,013 B2 | 3/2011 | Stevenson |
| 7,998,151 B2 | 8/2011 | St. Goar et al. |
| 8,066,650 B2 | 11/2011 | Lee et al. |
| 8,248,232 B2 | 8/2012 | Stevenson et al. |
| 8,253,555 B2 | 8/2012 | Stevenson et al. |
| 8,340,750 B2 | 12/2012 | Prakash et al. |
| 8,401,659 B2 | 3/2013 | Von Arx et al. |
| 8,529,474 B2 | 9/2013 | Gupta et al. |
| 8,622,936 B2 | 1/2014 | Schenberger et al. |
| 8,968,394 B2 | 3/2015 | Murad et al. |
| 9,101,264 B2 | 8/2015 | Acquista |
| 9,101,281 B2 | 8/2015 | Reinert et al. |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0049492 A1 | 12/2001 | Frazier et al. |
| 2002/0020074 A1 | 2/2002 | Love et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0036795 A1 | 2/2003 | Andersen et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |

| | | |
|---|---|---|
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0010296 A1 | 1/2004 | Swanson et al. |
| 2004/0019374 A1 | 1/2004 | Hojeibane et al. |
| 2004/0027306 A1 | 2/2004 | Amundson et al. |
| 2004/0034411 A1 | 2/2004 | Quijano et al. |
| 2004/0044406 A1 | 3/2004 | Woolfson et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0148017 A1* | 7/2004 | Stobie .................. A61F 2/2427 |
| | | 623/2.11 |
| 2004/0167573 A1 | 8/2004 | Williamson et al. |
| 2004/0186563 A1 | 9/2004 | Lobbi |
| 2004/0186565 A1 | 9/2004 | Schreck |
| 2004/0193261 A1 | 9/2004 | Berreklouw |
| 2004/0206363 A1 | 10/2004 | McCarthy et al. |
| 2004/0210304 A1 | 10/2004 | Seguin et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260389 A1 | 12/2004 | Case et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137690 A1 | 6/2005 | Salahieh et al. |
| 2005/0137692 A1 | 6/2005 | Haug et al. |
| 2005/0137695 A1 | 6/2005 | Salahieh et al. |
| 2005/0159811 A1 | 7/2005 | Lane |
| 2005/0165479 A1 | 7/2005 | Drews et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0216079 A1 | 9/2005 | MaCoviak |
| 2005/0222674 A1 | 10/2005 | Paine |
| 2005/0234546 A1 | 10/2005 | Nugent et al. |
| 2005/0240263 A1 | 10/2005 | Fogarty et al. |
| 2005/0251252 A1 | 11/2005 | Stobie |
| 2005/0261765 A1 | 11/2005 | Liddicoat |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058871 A1 | 3/2006 | Zakay et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0095125 A1 | 5/2006 | Chinn et al. |
| 2006/0122634 A1 | 6/2006 | Ino et al. |
| 2006/0149360 A1 | 7/2006 | Schwammenthal et al. |
| 2006/0154230 A1 | 7/2006 | Cunanan et al. |
| 2006/0167543 A1 | 7/2006 | Bailey et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0207031 A1 | 9/2006 | Cunanan et al. |

(56)  References Cited

U.S. PATENT DOCUMENTS

| 2006/0241745 | A1 | 10/2006 | Solem |
| 2006/0259136 | A1 | 11/2006 | Nguyen et al. |
| 2006/0271172 | A1 | 11/2006 | Tehrani |
| 2006/0271175 | A1 | 11/2006 | Woolfson et al. |
| 2006/0287717 | A1 | 12/2006 | Rowe et al. |
| 2006/0287719 | A1 | 12/2006 | Rowe et al. |
| 2007/0005129 | A1 | 1/2007 | Damm et al. |
| 2007/0010876 | A1 | 1/2007 | Salahieh et al. |
| 2007/0016285 | A1 | 1/2007 | Lane et al. |
| 2007/0016286 | A1 | 1/2007 | Herrmann et al. |
| 2007/0016288 | A1 | 1/2007 | Gurskis et al. |
| 2007/0043435 | A1 | 2/2007 | Seguin et al. |
| 2007/0078509 | A1 | 4/2007 | Lotfy |
| 2007/0078510 | A1 | 4/2007 | Ryan |
| 2007/0100440 | A1 | 5/2007 | Figulla et al. |
| 2007/0129794 | A1 | 6/2007 | Realyvasquez |
| 2007/0142906 | A1 | 6/2007 | Figulla et al. |
| 2007/0142907 | A1 | 6/2007 | Moaddeb et al. |
| 2007/0150053 | A1 | 6/2007 | Gurskis et al. |
| 2007/0156233 | A1 | 7/2007 | Kapadia et al. |
| 2007/0162103 | A1 | 7/2007 | Case et al. |
| 2007/0162107 | A1 | 7/2007 | Haug et al. |
| 2007/0162111 | A1 | 7/2007 | Fukamachi et al. |
| 2007/0179604 | A1 | 8/2007 | Lane |
| 2007/0185565 | A1 | 8/2007 | Schwammenthal et al. |
| 2007/0198097 | A1 | 8/2007 | Zegdi |
| 2007/0203575 | A1 | 8/2007 | Forster et al. |
| 2007/0203576 | A1 | 8/2007 | Lee et al. |
| 2007/0213813 | A1 | 9/2007 | Von Segesser et al. |
| 2007/0225801 | A1 | 9/2007 | Drews et al. |
| 2007/0233237 | A1 | 10/2007 | Krivoruchko |
| 2007/0239266 | A1 | 10/2007 | Birdsall |
| 2007/0239269 | A1 | 10/2007 | Dolan et al. |
| 2007/0239273 | A1 | 10/2007 | Allen |
| 2007/0255398 | A1 | 11/2007 | Yang et al. |
| 2007/0260305 | A1 | 11/2007 | Drews et al. |
| 2007/0265701 | A1 | 11/2007 | Gurskis et al. |
| 2007/0270944 | A1 | 11/2007 | Bergheim et al. |
| 2007/0282436 | A1 | 12/2007 | Pinchuk |
| 2007/0288089 | A1 | 12/2007 | Gurskis et al. |
| 2008/0033543 | A1 | 2/2008 | Gurskis et al. |
| 2008/0046040 | A1 | 2/2008 | Denker et al. |
| 2008/0119875 | A1 | 5/2008 | Ino et al. |
| 2008/0154356 | A1 | 6/2008 | Obermiller et al. |
| 2008/0319543 | A1 | 12/2008 | Lane |
| 2009/0036903 | A1 | 2/2009 | Ino et al. |
| 2009/0192599 | A1 | 7/2009 | Lane et al. |
| 2010/0049313 | A1 | 2/2010 | Alon et al. |
| 2010/0145438 | A1 | 6/2010 | Barone |
| 2010/0256723 | A1 | 10/2010 | Murray |
| 2012/0022641 | A1 | 1/2012 | Bergin et al. |
| 2012/0123284 | A1 | 5/2012 | Kheradvar |
| 2012/0296382 | A1 | 11/2012 | Shuros et al. |
| 2013/0144379 | A1 | 6/2013 | Najafi et al. |
| 2014/0128964 | A1 | 5/2014 | Delaloye |
| 2014/0188221 | A1 | 7/2014 | Chung et al. |
| 2014/0364707 | A1 | 12/2014 | Kintz et al. |
| 2015/0045635 | A1 | 2/2015 | Tankiewicz et al. |
| 2015/0313711 | A1* | 11/2015 | Chang .................... A61F 2/243 623/2.11 |
| 2016/0045316 | A1 | 2/2016 | Braido et al. |
| 2016/0113763 | A1 | 4/2016 | Green et al. |
| 2016/0199185 | A1 | 7/2016 | Murad et al. |

FOREIGN PATENT DOCUMENTS

| SU | 1116573 | A1 | 7/1985 |
| SU | 1697790 | A1 | 12/1991 |
| WO | 9213502 | A1 | 8/1992 |
| WO | 9742871 | A1 | 11/1997 |
| WO | 2013165937 | A1 | 11/2013 |

* cited by examiner

AORTA

PULMONARY
ARTERY

LEFT
ATRIUM

RIGHT
ATRIUM

MITRAL
VALVE

LEFT
VENTRICLE

AORTIC
VALVE

TRICUSPID
VALVE

RIGHT
VENTRICLE

PULMONARY
VALVE

FIG.5A
FIG.5B
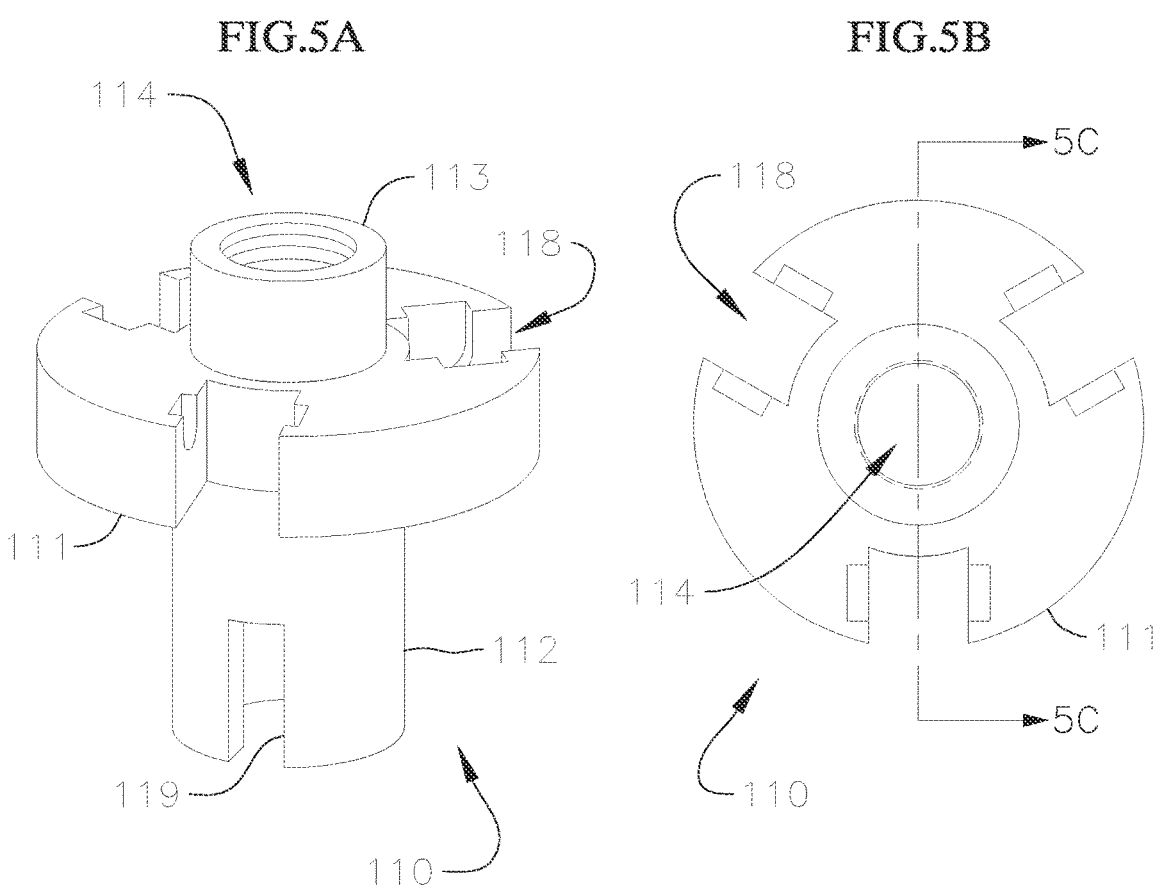
FIG.5C
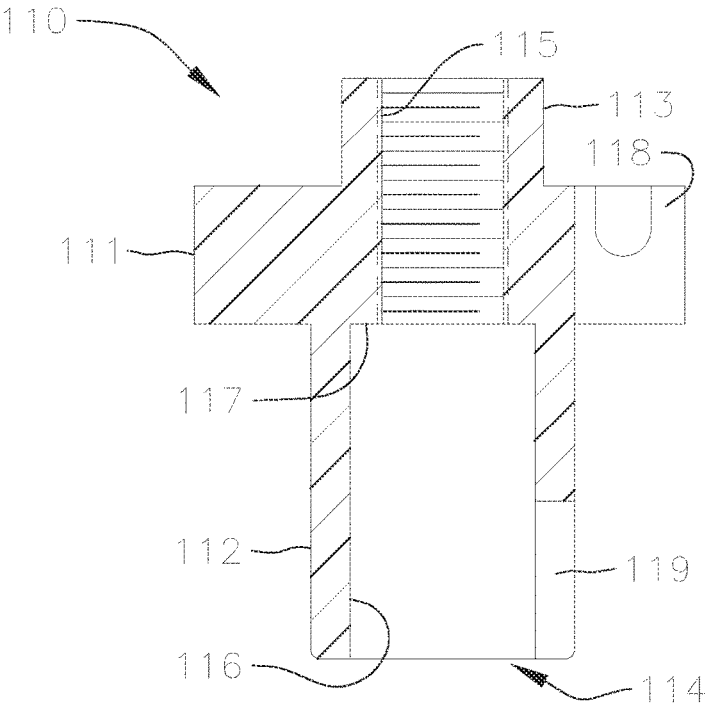

120

126

124

121

122

125

123

131

130

141

143

142

140

1

PROSTHETIC VALVE HOLDERS WITH AUTOMATIC DEPLOYING MECHANISMS

CROSS REFERENCE TO RELATED APPLICATIONS

This application is a continuation of U.S. application Ser. No. 16/673,487, filed Nov. 4, 2019, now U.S. Pat. No. 11,376,125, which is a divisional of U.S. application Ser. No. 15/481,283, filed Apr. 6, 2017, now U.S. Pat. No. 10,463,485, the entire disclosures which are incorporated by reference for all purposes.

BACKGROUND

Technical Field

The present disclosure generally concerns medical devices, deployment mechanisms, and methods for deploying such medical devices. More specifically, the disclosure relates to surgical replacement of heart valves that have malformations and/or dysfunctions. Embodiments of the invention relate to holders for facilitating the implantation of bioprosthetic replacement heart valves at such native heart valves, and methods of using the holders to facilitate implantation of the replacement valves.

Description of Related Art

Referring first to FIG. 1, the human heart is generally separated into four pumping chambers which pump blood through the body. Each chamber is provided with its own one-way exit valve. The left atrium receives oxygenated blood from the lungs and advances the oxygenated blood to the left ventricle through the mitral (or bicuspid) valve. The left ventricle collects the oxygenated blood from the left atrium and pushes it through the aortic valve to the aorta, where the oxygenated blood is then distributed to the rest of the body. Deoxygenated blood from the body is then collected at the right atrium and advanced to the right ventricle through the tricuspid valve. The right ventricle then advances the deoxygenated blood through the pulmonary valve and the pulmonary artery to the lungs to again supply the blood with oxygen.

Each of the valves associated with the chambers of the heart are one-way valves that have leaflets to control the directional flow of the blood through the heart, and to prevent backflow of the blood into other chambers or blood vessels that are upstream of the particular chamber. The valves are each supported by an annulus having a dense fibrous ring attached either directly or indirectly to the atrial or ventricular muscle fibers. When a valve become diseased or damaged, leakage or regurgitation may occur, where some of the blood travels back upstream through the diseased or damaged valve, and the efficiency and/or general functionality of the heart may be compromised.

Various surgical techniques can be performed to repair or replace a diseased or damaged valve. In some valve replacement procedures, the leaflets of the diseased or damaged native valve are first removed to prepare the valve annulus for receiving the prosthetic replacement valve. FIG. 2 shows an example of one type of popular prosthetic replacement valve 1 that is a tissue-type bioprosthetic valve generally constructed with natural-tissue valve leaflets 2, made for example, from porcine tissue or bovine pericardium, or from artificially synthesized tissue, that are mounted on a surrounding valve stent structure 3. The shape and structure of the leaflets 2 is supported by a number of commissure posts 4 positioned circumferentially around the valve stent 3. In these valves, a biocompatible cloth-covered suture or sewing ring 5 can also be provided on an inflow end of the stent structure 3 of the valve 1, for attachment to the native valve annulus. Such prosthetic valves function much like natural human heart valves, where the leaflets coapt against one another to effect the one-way flow of blood.

When implanting a tissue type prosthetic valve as described above at a native valve annulus, a number of sutures may be involved in the attachment process, many of which may be pre-installed for providing a track on which the valve is advanced to and properly positioned at the implant site. Additional sutures may also be applied between the prosthetic valve and the heart walls after proper placement, to securely attach or hold the valve implant in place. Meanwhile, in some cases, the prosthetic valves are implanted through small access channels using one of various minimally invasive surgical procedures, where visibility at the implant site may be impeded or obstructed. In addition, depending on the direction of implantation, for example, with some mitral valve replacement procedures, commissure posts of the stent or frame, or other portions, of the prosthetic valve may be pointed distally and advanced on a blind side of the valve.

Each of the above factors may lead to tangling of the sutures with the valve prosthesis, most commonly with the commissure posts of the frame, since they provide a protrusion on which the sutures can easily loop around and tangle. This type of entanglement of sutures with prosthetic valves is referred to as "suture looping," which specifically refers to instances where a suture is inadvertently wrapped around one or more of the commissure post tips, where it can then migrate towards and damage the leaflets or interfere with proper leaflet coaptation or other valve operation when the sutures are tightened or secured, resulting in improper valve operation. In some cases, such tangling may not be apparent to the practitioner at the time of implantation, and will only be revealed some time later when valve operation is observed to be improper or other complications arise in the patient, in which case, it may be necessary to initiate another procedure to repair or replace the prosthetic valve.

In addition, for example with aortic valve replacement procedures, during surgical implantation of a prosthetic aortic valve, there is often very little space between the aortic sinus and the commissures of the prosthetic valve, which makes advancing the knots in the sutures used to attach the prosthesis to the aortic annulus very difficult. Some surgeons use their fingers to advance the knots towards the implant site, and in the process, may inadvertently bend and/or otherwise damage the commissure posts or other portions of the prosthetic valve, which then requires the use of an additional prosthesis and/or increased procedure time.

SUMMARY

Attempts have been made to resolve the issue of suture looping, some of which revolve around the holders which hold the prosthetic valves when they are delivered to the native valve annulus. In one example, a holder has a mechanism that urges the commissure posts of the prosthetic valve radially inwardly during delivery, so that the ends of the commissure posts are pointed inwards, to reduce the possibility of sutures catching against or looping around them. After the valve prosthesis is delivered to the implant site, the holder is removed, releasing and expanding the commissure posts to their original positions. However, although the commissure posts are biased inwardly during delivery, since the ends of the commissure posts remain free, these holders have not been fully effective in eliminating instances of suture looping.

Meanwhile, Edwards Lifesciences has developed another valve holder system, known as the Tricentrix holder system, specifically for use in mitral valve replacement procedures to protect the valve from suture looping during valve implantation. The system includes monofilament sutures that attach to both the holder and the commissures of the prosthetic valve, so that the sutures run over the outflow end of the valve between the ends of the commissures. When the holder is actuated, a central post extends distally through the prosthetic valve between the leaflets and pushes against the sutures that run across the middle of the valve between the commissures, pushing the sutures distally and causing an angled tent-like or "umbrella" effect on the sutures. The pressure on the sutures deflects the commissures slightly inwardly, while also forming angled surfaces or tracks with the sutures that slope outwardly from the central post to the commissure posts. These angled surfaces deflect any other sutures that might otherwise be looped over a commissure or leaflet away from the prosthetic valve.

Other holders have also been developed in an attempt to further reduce instances of suture looping. However, some of these holders are very complex, for example, incorporating various rotary mechanisms and line connections in addition to the original hold and release mechanisms, such that a number of additional steps must be taken by the practitioner to operate the holders correctly. Many of these holders have proven to be too complicated and/or prone to user error. Consequently, when practitioners use these holders improperly, suture looping still commonly occurs, while the implant process may also be further complicated by issues arising from user error.

In addition to the above, many of the newer holder designs also incorporate many additional parts that interact with one another or that must be assembled by the practitioner or other end user, which may also lead to additional complications. For example, where additional parts must be threaded into one another, cross-threading can occur when the threads of the various parts are inadvertently misaligned. This and/or other interactions between the additional parts may lead to increased possibility of the holder being damaged or breaking, and of loose fragments being generated.

Features of the invention provide for new holder systems and methods of using the holder systems, which reduce or eliminate the occurrence of suture looping or other damage to the prosthetic valves during implantation. Operation of the holders is also simplified, where the additional features of the holders can be integrated for deployment or actuation automatically when performing existing steps already well-known by users, for example, via a step of attaching the holder to a delivery handle, thereby reducing or eliminating mistakes caused by user error. The holders can also have a reduced number of parts and/or provide for integrated alignment features or other safety features, so that cross-threading or other damaging interactions between parts can also be prevented. These holders can also be made at similar or reduced costs compared to existing holders.

In one embodiment of the invention, a valve holder is configured to be attached to a delivery handle and to a prosthetic heart valve including a plurality of commissure posts and a plurality of flexible leaflets connected to the commissure posts. The valve holder includes a body having a first end, a second end, and a central axis extending between the first and second ends, where the body includes a first portion at the first end and a second portion at the second end with an outer width that is smaller than an outer width of the first portion, where a coaxial bore extends through the body, and where a first region of the bore has an engagement portion for engaging the delivery handle. The valve holder also includes a plurality of arms connected to the first portion of the body and extending axially from the first portion towards the second end of the body, a plunger positioned in the bore of the body, where a first portion of the plunger is configured to extend at least partially into the first region of the bore, and a plurality of sutures respectively connected between each arm and the plunger. In a first configuration, the plunger is at a first position where the first portion of the plunger extends into the first region of the bore, the sutures extend substantially radially from the plunger to respective ones of the arms, and free ends of the arms are positioned at a first radial distance from the central axis of the body. In a second configuration, the plunger is at a second position closer to the second end of the body, at least part of the sutures are displaced by the plunger towards the second end of the body, and the arms are pivoted radially inwardly by the sutures such that the free ends of the arms are positioned at a radial distance from the central axis of the body that is less than the first radial distance to inwardly deflect commissure posts of the prosthetic heart valve that are attached to free ends of the arms.

In another embodiment of the invention, a valve holder is configured to be attached to a delivery handle and to a prosthetic heart valve comprising a plurality of commissure posts and a plurality of flexible leaflets connected to the commissure posts. The valve holder includes a hub having a first end, a second end, and a central axis extending between the first and second ends, where the hub includes a first portion at the first end and a second portion extending from the first portion towards the second end, where a coaxial bore extends through the second portion of the hub, and where a first region of the bore has an engagement portion for engaging the delivery handle. The valve holder also includes a post including a longitudinally extending central body configured to be positioned in the bore and to extend at least partially into the first region of the bore, and a plurality of sutures configured to connect to and extend from the first end of the hub in a direction away from the second end of the hub and to engage respective commissure posts of the prosthetic heart valve, where the sutures form a crossing region on the central axis at a first distance from the first end of the hub. In a first configuration, the central body of the post extends into the first region of the bore and where a first end of the post is at a first position that is spaced apart from the crossing region of the sutures. In a second configuration, the post is positioned farther away from the second end of the hub, and the first end of the post is at a second position where the first end of the post engages the crossing region of the sutures and axially displaces the crossing region of the sutures away from the hub to inwardly deflect commissure posts of the prosthetic heart valve that are attached to the sutures.

In yet another embodiment of the invention, a system is configured to deliver a prosthetic heart valve including a plurality of commissure posts and a plurality of flexible leaflets connected to the commissure posts to an implant site. The system includes a valve holder configured to be attached to the prosthetic heart valve and a delivery handle for advancing the valve holder and the prosthetic heart valve to the implant site. The valve holder includes a holder body having a coaxial bore extending therethrough, where a first region of the bore has an engagement portion, a plunger configured to be positioned in the bore and to extend at least partially into the first region of the bore, and a plurality of sutures configured to be axially displaced by the plunger. The delivery handle includes an engagement portion configured to engage the engagement portion at the first region of the bore of the valve holder. When the engagement portions of the valve holder and the delivery handle are engaged, the delivery handle adjusts the valve holder to a deployed configuration by moving a position of the plunger to axially displace the sutures and to inwardly deflect commissure posts of the prosthetic heart valve that are attached to the valve holder.

According to embodiments of the invention, holders for prosthetic valve delivery reduce or eliminate occurrences of suture looping and/or other damage to the valves when the valves are implanted, while the mechanisms for deploying these features are integrated into the holders in a way that makes it easier for end users to use and deploy.

BRIEF DESCRIPTION OF THE DRAWINGS

Further features and advantages of the invention will become apparent from the description of embodiments using the accompanying drawings. In the drawings:

FIGS. 5A to 5C respectively show a perspective view, a top view, and a cross-sectional view of a body of the valve holder of FIGS. 3 and 4;

DETAILED DESCRIPTION

Disclosed herein are various valve holders for assisting in the delivery and implantation of prosthetic heart valves at an implant site, and methods for preparing the prosthetic heart valves for such procedures. Embodiments of the valve holders reduce occurrences of various complications that may arise during implantation, while remaining simple for end users to use. By providing these improved valve holders, damage to the prosthetic valves during surgical procedures can be reduced, and additional costs for extended or additional procedures and replacement valves can be avoided.

The valve holders disclosed herein are particularly useful for avoiding suture looping and other valve damage during advancement of the prosthetic valves to the implant sites, as well as during final suturing of the valves at the native valve annulus. In procedures where commissure posts of the prosthetic valve point proximally towards the practitioner, for example, in many aortic valve replacement procedures, valve holders according to embodiments of the invention protect the valve stent from sutures as well as from the practitioner's extremities and other tools during attachment of the valve at the implant site. Meanwhile, in procedures where commissure posts of the prosthetic valve point distally, for example, in many mitral valve replacement procedures, the commissure posts point in the direction of valve advancement and may be more prone to suture looping or other entangling. In these cases, valve holders according to embodiments of the invention can urge the commissure posts inwards and can also provide angled sutures or wires that form tracks that deflect other sutures away from the prosthetic valve. Each of the presented embodiments also effect automatic deployment or actuation of the respective valve holders to their deployed positions, using steps that are already associated with handling of existing valve holders.

In this fashion, ease of use of the below described valve holders can be maintained, while user error can be minimized.

Valve holders according to embodiments of the invention can also apply or be modified to apply to procedures for replacing heart valves other than at the aortic and mitral positions. For example, a valve holder according to an embodiment of the invention can be utilized for holding a prosthetic valve for replacing a damaged or diseased tricuspid valve, and can be selected depending on the direction of delivery of the prosthetic valve.

Figures 3, 4:
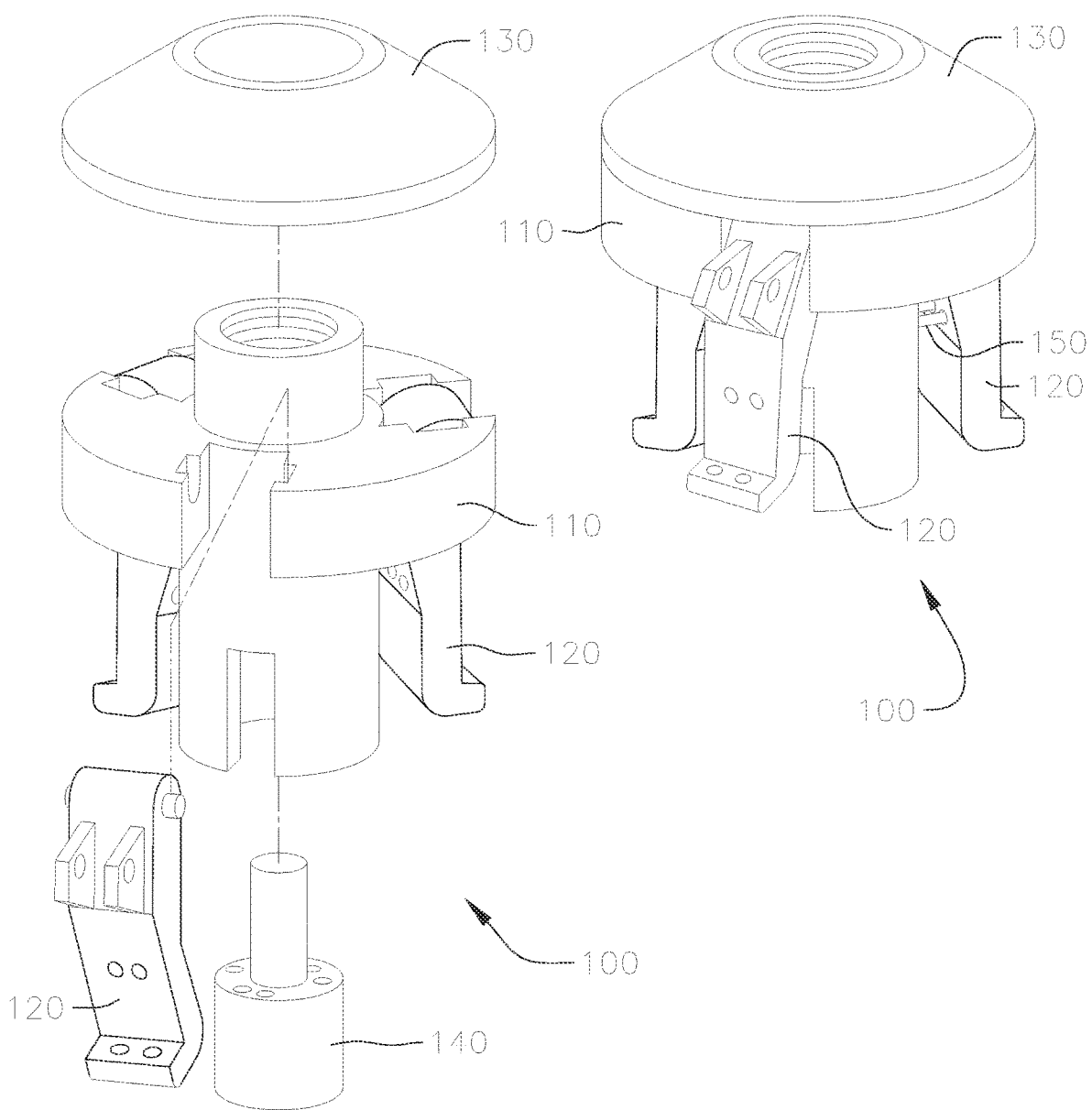
FIG. 3 shows an exploded perspective view of a valve holder for a prosthetic aortic valve according to an embodiment of the invention.
FIG. 4 shows a perspective view of the valve holder of FIG. 3 in an assembled state.

FIG. 3 shows an exploded perspective view of a valve holder according to an embodiment of the invention, and FIG. 4 shows a perspective view of the valve holder of FIG. 3 in an assembled state. The valve holder in FIGS. 3 and 4 can be used, for example, for delivering a prosthetic aortic valve to the aortic position.

The valve holder 100 in FIGS. 3 and 4 includes a body 110, a plurality of arms 120, a cap 130, and a plunger 140. In the embodiment shown, the valve holder includes three arms 120, but in other embodiments, valve holders can include more or less arms, depending on the prosthetic valve the valve holder is intended to hold, where the number of arms generally corresponds to the number of commissure posts on the prosthetic valve. The arms 120 are attached to an upper portion of the body 110, and the arms 120 and body 110 are held together with the cap 130. Meanwhile, the plunger 140 is positioned in a bore of the body 140. As can be seen in FIG. 4, a plurality of connections 150 (e.g., via suture loops or ties, other flexible material, or other attachment mechanisms) respectively extend radially inwards and extend through a lower portion of the body 110 for interaction with the plunger 140, as discussed in greater detail below.

The body 110 of the valve holder 100 is shown in greater detail in FIGS. 5A to 5C. The body 110 includes a disk-shaped or cylindrically shaped central portion 11 and a lower cylindrical portion 112 that has an outer diameter that is less than the outer diameter of the central portion 111. In some embodiments, the body 110 also includes an upper cylindrical portion 113 that also has an outer diameter that is less than the outer diameter of the central portion in. Meanwhile, while the respective portions 111, 112, 113 of the body 110 are formed as cylindrical portions in the described embodiment, other embodiments may have one or more portions that have different cross-sectional shapes.

A through bore 114 extends through a central axis of the body 110. The through bore 114 has an upper region 115 with an inner engagement structure, such as an inner thread, and a lower region 116 that has a substantially cylindrical inner surface. The upper region 115 of the bore 114, including the inner engagement structure, extends from an upper end of the body 110 down to approximately where the central portion in and the lower portion 112 meet, while the lower region 116 of the bore 114 extends substantially through the lower portion 112. In the illustrated embodiment, the lower region 116 of the bore 114 is slightly wider than the upper region 115 of the bore 114, forming an abutting surface 117 therebetween. The abutting surface 117 serves as a stop for the plunger 140, as described in greater detail below.

A plurality of engagement portions 118 are formed on an outer surface of the central portion in of the body 110. Each of the engagement portions 118 is configured to receive a corresponding engagement portion of an arm 120 of the valve holder 100, to attach the arms 120 to the body 110. Therefore, the number of the engagement portions 118 corresponds to the number of arms 120 desired on the valve holder 100. In the illustrated embodiment, the valve holder 100 includes three engagement portions 118 for respectively receiving three arms 120. The engagement portions 118 are arranged as recesses that receive correspondingly shaped enlarged ends of the arms 120, where the enlarged ends of the arms 120 can be inserted, for example, from upper openings of the recesses and rest on lower surfaces formed by the recesses. When the enlarged ends of the arms are held in the engagement portions 118 in this manner, the cap 130 can then be attached to the top or proximal end of the body 110 to lock the body 110 and the arms 120 together. Meanwhile, in other embodiments, the engagement portions 118 and arms 120 can be designed in any number of different ways, so long as hinge joints are formed between the body 110 and the arms 120, or so long as the connections allow for movement or pivoting of the free ends of the arms 120 radially inwards towards a central axis of the valve holder 100.

The lower portion 112 of the body also has longitudinal slits 119 that are radially aligned with the engagement portions 118, so as to also align with the arms 120. The slits 119 are generally rectangular in shape and extend from a free end of the lower portion 112 to a distance from where the central portion 111 and the lower portion 112 of the body 110 meet. This distance can correspond, for example, to a length of a larger portion of the plunger 140, as will be described in greater detail below.

Figures 6, 7, 8:
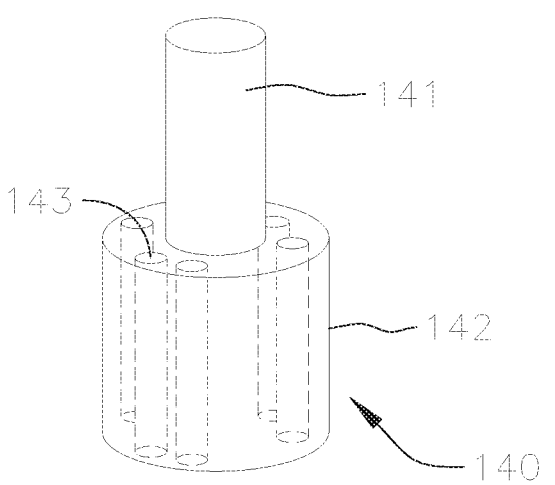
FIG. 6 shows a perspective view of one arm of the valve holder of FIGS. 3 and 4.
FIG. 7 shows a perspective view of a cap of the valve holder of FIGS. 3 and 4.
FIG. 8 shows a perspective view of a plunger of the valve holder of FIGS. 3 and 4.

A perspective view of one of the arms 120 is shown in FIG. 6. The arm 120 has an upper portion 121 and a lower portion 122. Either the upper portion 121 or the lower portion 122, or both, can be tapered so that the arm 120 reduces in width towards the lower portion 122. The lower portion 122 can also be slightly angled relative to the upper portion 121, so that when the arm 120 is attached to the body 110, the lower portion 122 is angled slightly inwardly to reduce a profile or size of the valve holder 100.

A projection 123 that projects in a direction transverse to a longitudinal axis of the arm 120 is formed at the free end of the lower portion 122. The projection 123 may include one or more apertures or other features for engaging or passing through of a suture that connects the arm 120 to a corresponding commissure of the prosthetic valve. Near an opposite end of the arm 120, a second projection or engagement feature 124 can be included for providing a second attachment point for the suture that connects the prosthetic valve commissure. The second projection 124 in the instant embodiment is formed by one or more tabs with through holes for threading the suture.

Meanwhile, near a center of the arm 120, approximate where upper portion 121 and lower portion 122 meet, one or more additional through holes or bores 125 is formed transversely through the arm 120. In some embodiments, the through holes 125 are formed slightly lower, approximately two-thirds of the way down from the top ends of the arms 120. The through holes 125 extend in a direction similar to the direction of extension of the projections 123. The through holes 125 are configured to connect the arm 120 to the plunger 140 located in the bore 114 of the body 110 via the same or a separate suture as the one described above. The position of the through holes 125 generally align longitudinally with closed ends of the longitudinal slits 119 on the lower portion 112 of the body 110 when the arms 120 are attached to the body 110. In this manner, when the valve holder 100 is assembled and in a first un-deployed configuration, described in greater detail below, the sutures connecting the arms 120 to the plunger 140 are configured to extend substantially horizontally or radially relative to the central axis of the valve holder 110.

Near the free end of the upper portion 121, the arms 120 also include projections 126 for engagement with the engagement recesses 118 on the central portion 11 of the body 110. The projections 126 are formed here as cylindrical knobs configured to fit in the recesses 118 on the body 110, but as noted above, any of various other complementary engagement shapes and/or features can instead be used for the engagement features 118 and 126, so long as the resulting connections allow for movement or pivoting of the free ends of the arms 120 radially inwards towards the central axis of the valve holder 100.

A perspective view of the cap 130 is provided in FIG. 7. The cap 130 has a substantially circular shape, and has a slightly tapered outer surface that widens towards an end that is configured to face the body 110 when the cap 130 is attached to the body 110. In general, an outer profile of the cap 130 at the end that connects to the body 110 corresponds in size and shape to the outer profile of the central portion in of the body 110, so that a smooth transition is formed between the cap 130 and the body 110 when the parts are connected. For embodiments where the body 110 has an upper portion 113, the cap 130 may have a complementary through bore 131 to allow the cap 130 to be fitted around the upper portion 113. The cap 130 connects to the top of the body 110, for example, by a press-fit or snap engagement (not shown). Engagement portions can be provided, for example, on a top surface of the central portion in, on the upper portion 113, or both. However, any other type of connection that securely connects or mates the cap 130 to the body 110 can be utilized. For example, the cap 130 can be attached to the body 110 with an adhesive. In some embodiments, the cap 130 also has three grooves on its bottom surface that are configured to align with the engagement portions 118 on the body 110 to complete cavities in which the projections 126 of the arms 120 respectively connect, and along which the projections 126 and the rest of the upper portions 121 of the arms 120 can be guided when the arms 120 are pivoted at the connections.

FIG. 8 shows a perspective view of the plunger 140. The plunger 140 includes an upper portion 141 and a lower portion 142. In the illustrated embodiment, both the upper portion 141 and the lower portion 142 are substantially cylindrically shaped, but one or both of the portions can be formed in different shapes in other embodiments. The upper portion 141 is smaller than the lower portion 142 in diameter. The plunger 140 is sized to fit into the bore 114 of the body 110, and can be inserted through the bottom opening of the body 110 and held in the lower region 116 of the bore, with the upper portion 141 of the plunger 140 directed towards the top or proximal end of the body 110.

The diameter of the upper portion 141 of the plunger 140 is smaller than the inner diameter of the upper region 115 of the bore 114, so that the upper portion 141 of the plunger 140 can extend into the upper region 115 of the bore 114. Meanwhile, the diameter of the lower portion 142 of the plunger 140 is smaller than the inner diameter of the lower region 116 of the bore 114, but is larger than the inner diameter of the upper region 115 of the bore 114. Therefore, the lower portion 142 of the plunger 140 abuts against the abutting surface 117 formed in the body 110, which forms a stop against further upward movement of the plunger 140 when it is held in the bore 114.

A series of through holes 143 or other engagement features are provided on the lower portion 142 of the plunger 140. The through holes 143 are configured for attaching sutures that extend between the plunger 140 and each of the arms 120. The through holes 143 are therefore positioned radially around the lower portion 142 of the plunger 140 at positions corresponding to the arms 120 and the slits 119 on the body 110, so that each of the sutures can pass through a respective one of the slits 119.

Figures 9A, 9B:
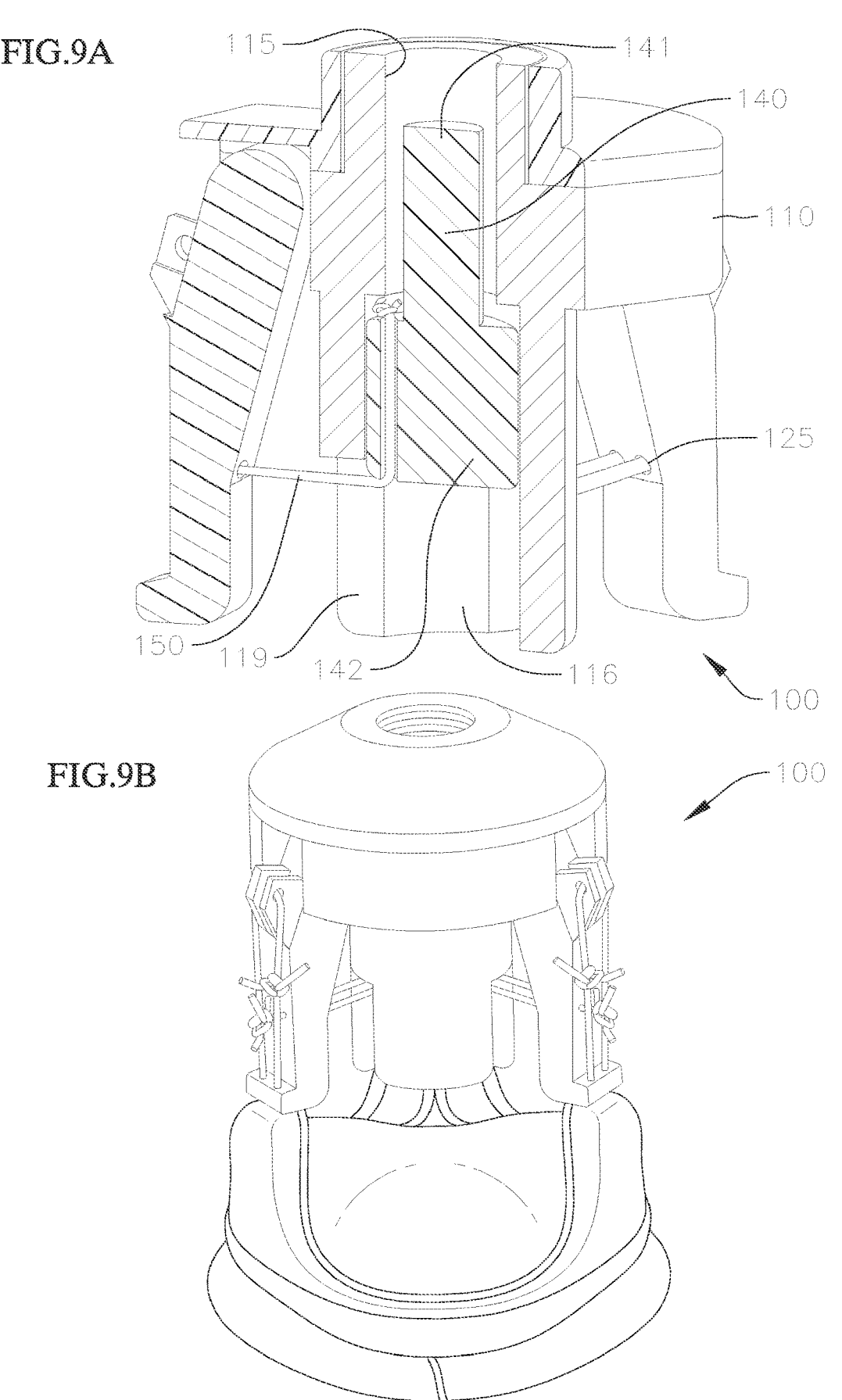
FIG. 9A shows a perspective view with a partial cross-section of the valve holder of FIGS. 3 and 4 in a first, un-deployed, configuration.
FIG. 9B is an image showing the valve holder in the first configuration with a replacement valve attached thereto.

FIG. 9A shows a perspective view of the assembled valve holder 100 with a partial cross-section showing interaction between the various parts. The valve holder 100 in FIG. 9A is in a first, un-deployed, configuration, where the valve holder 100 has not been attached to a separate handle that is used to facilitate delivery of the valve holder 100 and attached prosthetic valve to the implant site, and where the arms 120 have not yet been urged radially inwards.

As can be seen in FIG. 9A, the upper ends of the arms 120, with the projections 126, have been inserted into the engagement recesses 118 on the central portion 11 of the body 110, and the cap 130 has been attached to the upper end of the body 110 to secure the arms 120 to the body 110. Meanwhile, the plunger 140 is being held at a high position in the lower region 116 of the bore 114 of the body 110, with the upper portion 141 of the plunger 140 extending into the upper region 115 of the bore 114, and the lower portion 142 of the plunger 140 abutting against the surface 117 in the bore 114. In this position, a bottom end of the plunger 140 generally aligns axially with the tops of the slits 119 on the body 110 and the bores 125 on the arms 120, so that the suture loops or connections 150 running between the plunger 140 and each of the arms 120 extend substantially horizontally or radially relative to the central axis of the valve holder 110. The sutures 150 are attached, for example, by threading through the bores 125 on the arms 120 and the through holes 143 on the plunger 140. Since a length of each of the sutures 150 between the plunger 140 and the arms 120 remains fixed, this horizontal orientation of the sutures 150 represents the configuration of the valve holder 100 where the arms 120 are pivoted outwardly at a greatest distance. In some embodiments, the arms 120 may be continually outwardly biased, for example, based on the construction of the connection between the arms 120 and the body 110, while the sutures 150 prevent the arms 120 from pivoting outwardly any further. Therefore, the valve holder 100 can be held in the un-deployed position, where the sutures can 150 remain tensioned and the plunger 140 is held in and prevented from falling out of the body 110, when no external forces are acting on the valve holder 100.

In addition to the above, additional sutures or other flexible material or attachment mechanisms are utilized to attach the valve holder 100 to a prosthetic valve. FIG. 9B is an image showing a valve holder 100 in the first, un-deployed position and attached to a prosthetic valve via a series of additional sutures running on an outer surface of the arms 120. These additional sutures can be extensions of the sutures 150 running between the plunger 140 and the arms 120, or can be separate sutures used specifically for attaching the prosthetic valve. The additional sutures extend from the tabs 124 through the apertures on projections 123 and are sewn to or otherwise attach to the commissure posts on the prosthetic valve. In other embodiments, other attachment methods may be utilized, so long as the bottom ends of the arms 120 attach securely to the free ends of the commissure posts on the prosthetic valves, so that the two features can pivot radially inwards and outwards together, and where the connections are quickly and easily detachable by an end user.

Figures 10A, 10B:
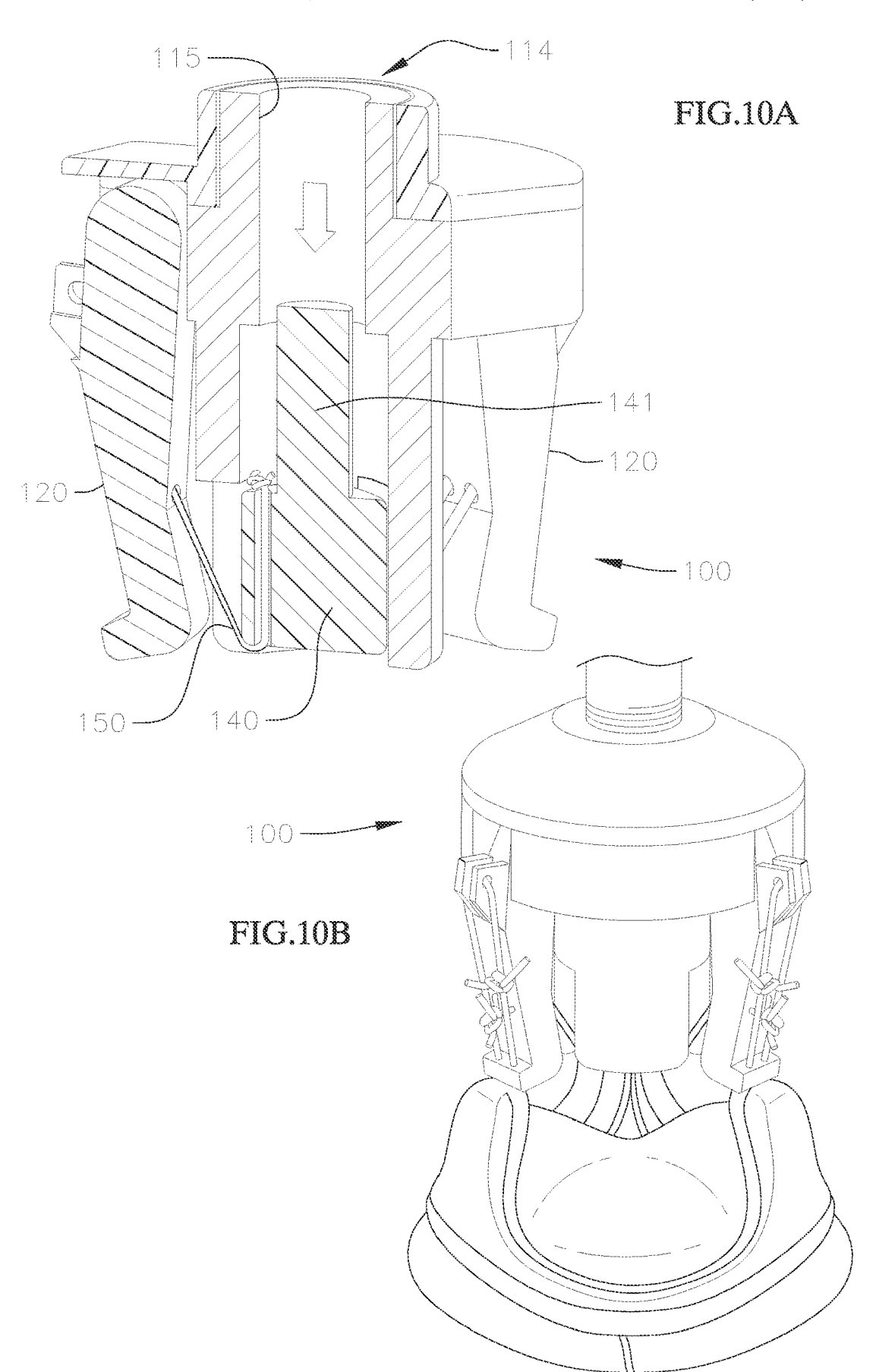
FIG. 10A shows a perspective view with a partial cross-section of the valve holder of FIGS. 3 and 4 in a second, deployed, configuration.
FIG. 10B is an image showing the valve holder in the second configuration with a replacement valve attached thereto.

FIG. 10A shows a perspective view of the valve holder 100 with a partial cross-section showing the interactions between the various parts. The valve holder 100 in FIG. 10A has been moved or adjusted to a second, deployed configuration, where the plunger 140 has been pushed or urged axially downwardly to a low position towards the bottom opening of bore 114. This downward force can be applied to the top end of the upper portion 141 of the plunger 140, for example, by a separate extension handle (not shown) to which the valve holder 100 can be connected. Such handles are already readily used by practitioners to help navigation and delivery of existing valve holders to implant sites.

As discussed earlier, upper region 115 of bore 114 is threaded. The handle includes a corresponding thread for engaging the valve holder 100. The distal end of the handle provides an abutting end, such that advancement of the handle into the upper region 115 of the bore 114 will push the plunger 140 downwards out of the upper region 115 and towards the bottom opening of the bore 114, as illustrated by the downward arrow in FIG. 10A. When the plunger 140 is advanced downwards, the ends of sutures 150 connected to plunger 140 are tensioned and are also shifted downwards, while the axial position of the ends of the sutures 150 connected to arms 120 stays substantially the same, displacing the sutures 150 to an orientation where they extend downwardly at an angle towards the bottom end of the body 110. This, in turn, pulls or deflects the bottoms of the arms 120 radially inwardly, where the arms 120 pivot or rotate at the respective connections to the body 110.

FIG. 10B is an image showing the valve holder 100 connected to the prosthetic valve and actuated by the extension handle connected at the upper region 115 of the bore 114, so that the valve holder 100 is held in the second, deployed position. The arms 120 have been pivoted inwardly, which in turn urges and deflects the ends of the commissure posts of the prosthetic valve inwardly as well. The practitioner can then use the attached handle to maneuver the valve holder 100 and prosthetic valve to the implant site, and can further attach the prosthetic valve to the native valve annulus, for example, by tying suture knots, while the commissure posts on the prosthetic valve are deflected inwardly and held at a position that provides more space for maneuverability at the implant site. After the prosthetic valve has been securely attached at the implant site, the handle can then be detached, the valve holder 100 is automatically released from the deployed position via the detachment of the handle, the prosthetic valve returns to its original shape, and the valve holder 100 can then also be detached from the fully implanted prosthetic valve, for example, by untying or cutting the sutures connecting the valve to the valve holder 100.

When the prosthetic valve is advanced and held at the implant site in the deflected configuration, the inward deflection of the commissure tips protects the commissures from the practitioner and/or tools during suture tying, and also protects the commissure tips from entanglement. Actuation is simplified, since a same number of turns needed to connect the handle (e.g., six turns) will also fully and automatically actuate the valve holder 100. Meanwhile, since the valve holder 100 is automatically actuated to the deployed position when the handle is attached, a step that is already performed by an end user when implanting existing prosthetic valves, and is also automatically released back to the un-deployed position when the handle is removed, the end user does not need to learn or perform any additional steps to properly activate and deactivate the valve holder 100, thereby reducing the possibility of user error.

The embodiment of the valve holder 100 described above includes separate body 110, arms 120, and cap 130. However, in other embodiments, these components can be combined into fewer pieces, for example, a single piece to simplify the valve holder design. This can be achieved, for example, by molding the body and arms as one piece from a flexible material with living hinges where the arms attach to the body. Molding the body and arms as one piece would also obviate the need for a separate cap (which was used to secure the arms to the body in the above embodiment), or for any additional attachment means or adhesives. Such a valve holder would therefore only include two components, the modified body and plunger 140. Meanwhile, while the valve holder 100 described may be slightly larger than currently existing valve holders, various modifications can also be made to optimize or reduce the holder size to be comparable to existing valve holders. The height of the valve holder 100 can be shortened, for example, by shortening the arms 120, lowering the position of the central portion 11 on the body 110, and/or reducing the axial distance the plunger 140 travels to fully actuating or deploying the deflection mechanism. In addition, the connection points of the arms 120 to the body 110 can be moved radially inwards to reduce a diameter or width of the top of the valve holder 100, which could be beneficial by increasing visibility and/or proximal access or space to work for the practitioner. In another modification, a locking or holding mechanism, such as a small molded latch, can also be added to the plunger 140 or other component, to hold the valve holder 100 in the deployed or activated configuration, even after the extension handle is removed. This way, the handle can be removed to provide even more space for the practitioner to adjust or modify the positioning or attachment of the prosthetic valve, while the valve and holder are both still held in the deflected configuration. In yet another modified embodiment, the handle can be attached to a removable adapter that is a separate piece from other parts of the body, such that the adapter can be separated from the rest of the body when desired, in order to allow for easier removal of the handle, without having to unscrew the handle from the valve holder assembly. Such an adapter can be attached to the rest of the body, for example, by a suture or other tie-down, where cutting or undoing the suture would allow for easy removal of the adapter and the handle attached thereto, further simplifying use of the valve holder for the end user.

Figures 11, 12:
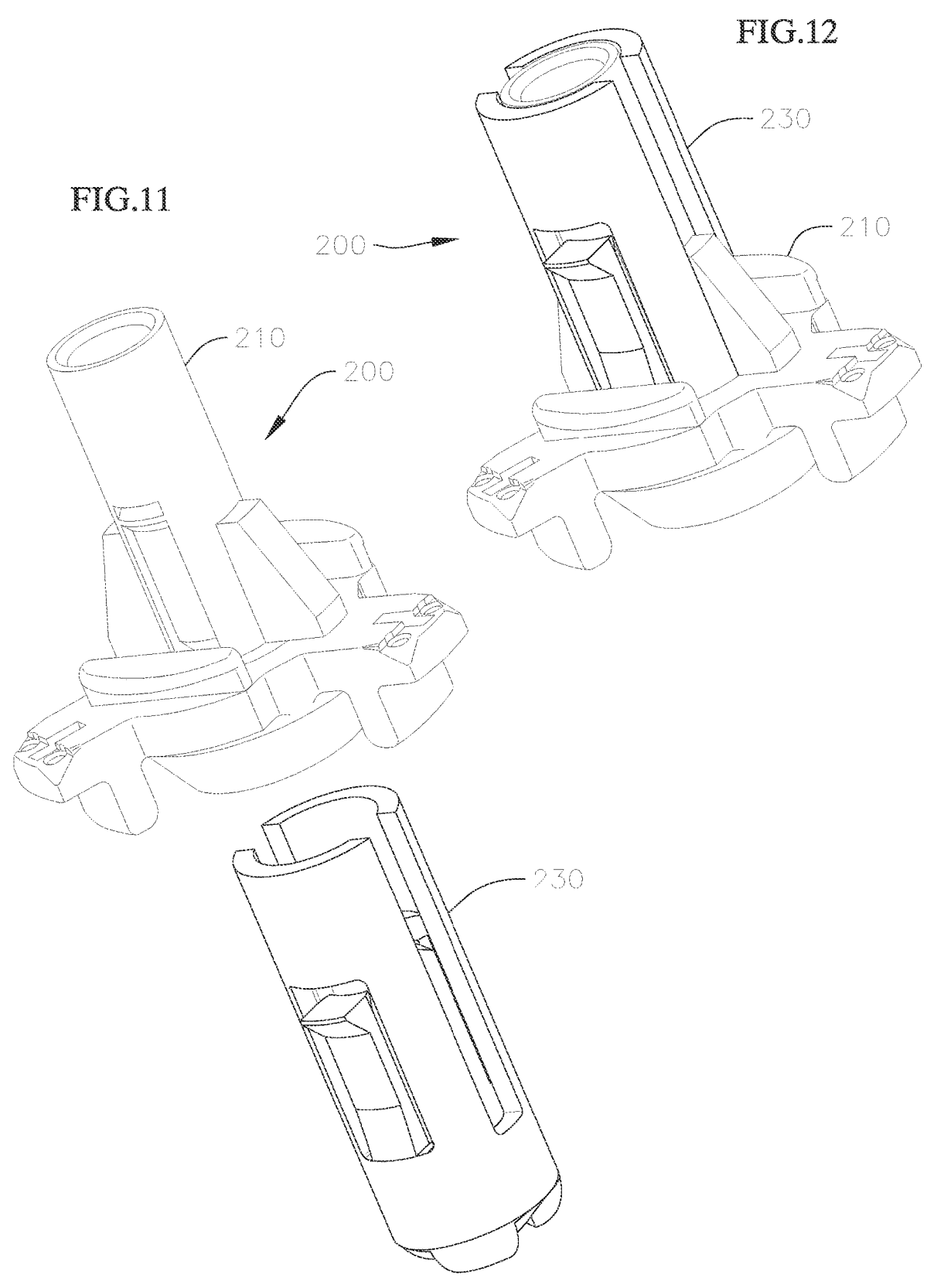
FIG. 11 shows an exploded perspective view of a valve holder for a prosthetic mitral valve according to an embodiment of the invention.
FIG. 12 shows a perspective view of the valve holder in FIG. 11 in an assembled state.

FIG. 11 shows an exploded perspective view of a valve holder according to another embodiment of the invention, and FIG. 12 shows a perspective view of the valve holder of FIG. 11 in an assembled state. The valve holder in FIGS. 11 and 12 can be used, for example, for delivering a prosthetic mitral valve to the mitral position.

Figure 1:
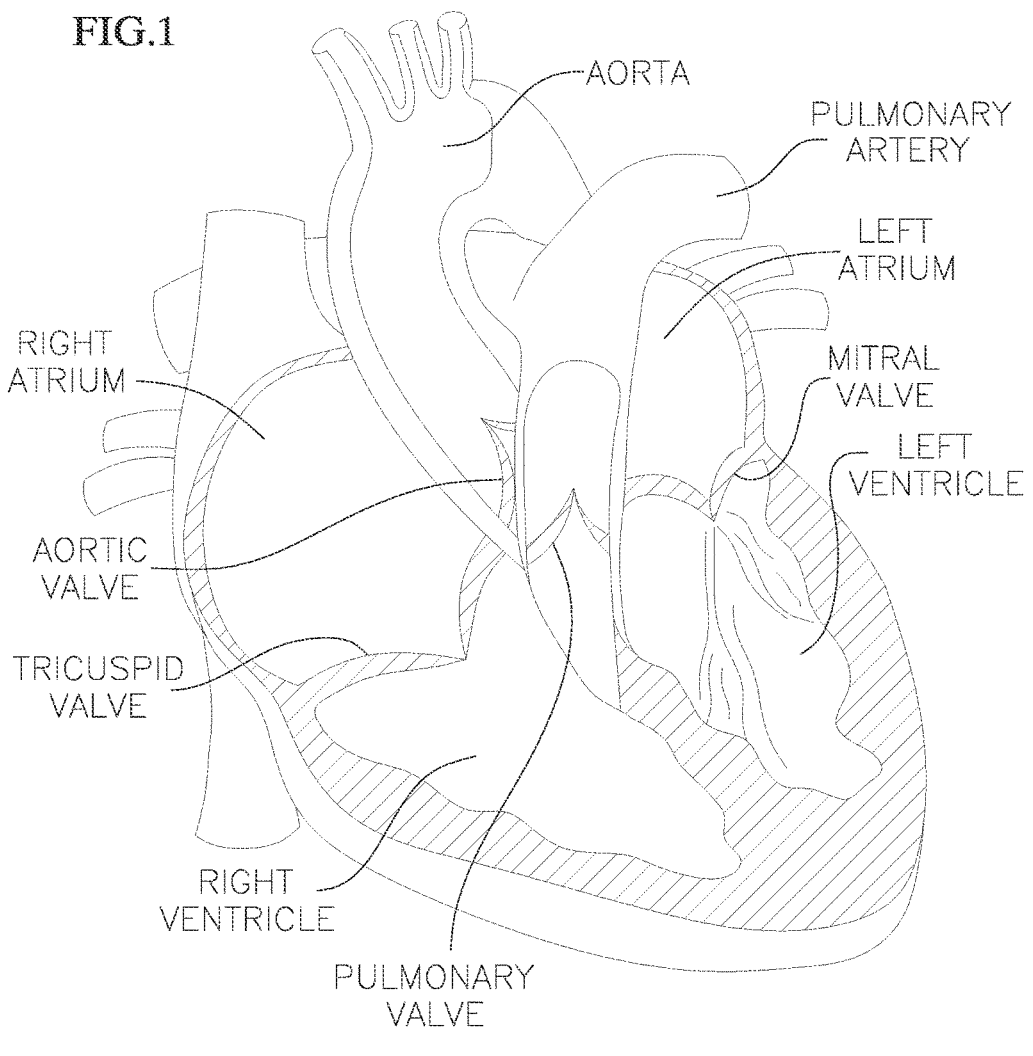
FIG. 1 shows a schematic cross-sectional view of a human heart.
Figure 2:
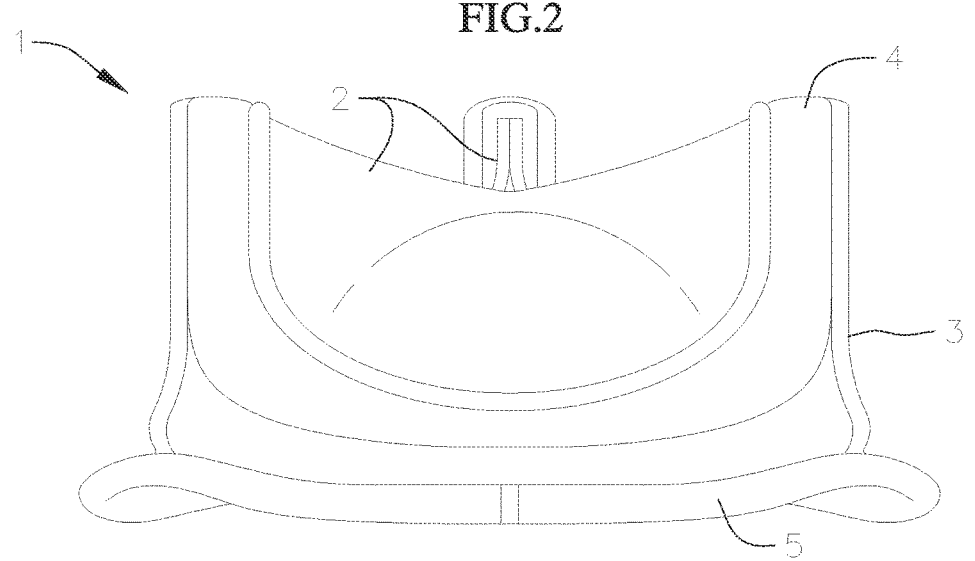
FIG. 2 shows a schematic perspective view of an example of a prosthetic valve that can be used with embodiments of the invention.

The valve holder 200 in FIGS. 11 and 12 has only two parts, a hub or holder body 210 and a post 230. The valve holder 200 is configured to attach to an inflow side of a prosthetic valve such as the prosthetic valve 1 discussed with respect to FIG. 2, so that at least part of the valve holder 200 extends through the central opening of the valve 1. Furthermore, the post 230 is movable relative to the hub or body 210, so that the post 230 can extend past an outflow end of the valve 1 when the valve holder 200 is attached to the valve 1, as discussed in greater detail below.

Figures 13A, 13B:
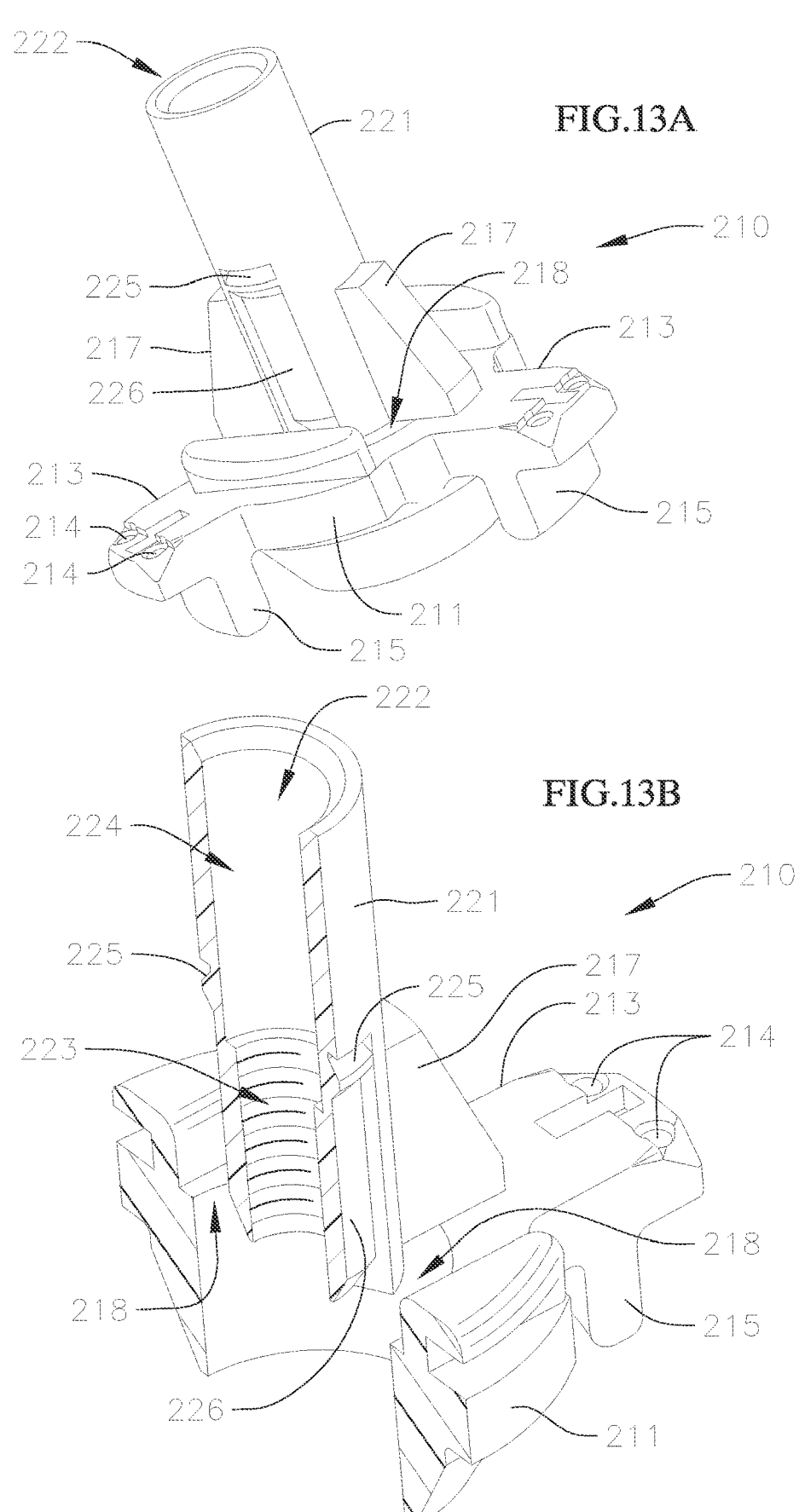
FIGS. 13A and 13B respectively show a perspective view and a cross-sectional view of a hub or holder of the valve holder of FIGS. 11 and 12.

The hub or holder body 210 is shown in greater detail in FIGS. 13A and 13B. The hub 210 includes a generally circular first portion 211 and a substantially cylindrical second portion 221 that is connected to and extends proximally from the first portion 211.

The first portion 211 of the hub 210 is sized and shaped to fit at least partially at or through an inflow opening of a prosthetic valve. In the embodiment shown, the first portion 211 includes three radial projections 213, each of which has one or more through holes or apertures 214 for threading sutures therethrough, as well as axial extensions 215 positioned radially inwardly from the apertures 214, for further supporting a shape of the prosthetic valve or for supporting inner surfaces of the commissure posts on the prosthetic valve. When a prosthetic valve is attached to the valve holder 200, an inflow end of the prosthetic valve rests on an upper surface of the first portion 211, while the axial extensions 215 extend a small distance into the valve and can apply a small radial outward pressure against the inner surface of the valve stent, to help hold the inflow end of the prosthetic valve stent at a desired shape. Meanwhile, the apertures 214 are positioned proximally relative to the prosthetic valve, and a series of sutures or suture loops extend from the apertures through the base of the valve stent and then through the commissures of the valves (as can best be seen in FIG. 16B), in order to help adjust a shape or deflection of the commissure posts of the attached valve. While a particular shape and specific features of the first portion 211 is shown in the embodiment discussed, the first portion can be formed in other shapes and with different features in other embodiments, so long as a connection to an associated prosthetic valve is easily and effectively facilitated.

One or more vertical struts or supports 217 extend radially between the first portion 211 and the second portion 221, to connect the second portion 221 to the first portion 211. Meanwhile, one or more circumferential gaps or recesses 218 is formed therebetween, e.g., in the regions where there are no supports 217. The gap or gaps 218 provide space through which a portion of the post 230 can extend, as discussed in greater detail below.

The second portion 221 of the hub 210 is formed generally as a tubular section that extends proximally from the first portion 211. The second portion 221 has a through bore 222 with a first region 223 positioned closer to the first portion 211, and a second region 224 positioned farther away from the first portion 211. In the embodiment shown, the first region 223 of the bore 222 has a smaller diameter than the second region 224 of the bore 222. In addition, the first region 223 of the bore 222 is threaded for attaching a threaded distal end of an extension handle (not shown) to the valve holder 200, while the second region 224 of the bore 222 provides a threading guide for insertion and guiding of the threaded end of the handle to the first region 223. An opening of the second region 224 of the bore 222 on a side opposite the first region 223 can also be tapered or beveled, for further facilitating and guiding the threaded end of the handle into the bore 222.

An outer surface of the second portion 221 of the hub 210 is substantially smooth to facilitate sliding of the post 230 over the second portion 221. The outer surface of the second portion 221 may include one or more grooves or detents 225 for engaging corresponding latches located on the post 230. The embodiment shown includes two detents 225 located circumferentially opposite to or across from one another. The detents 225 can have a triangular cross-section, with a flat surface for providing an abutment for the latches, and a sloping surface that widens towards the first portion 211 of the hub 210, where the latches can flex radially outwardly to pass over the sloping surfaces when the post 230 is moved distally relative to the hub 210. In addition, each of the detents 225 may be connected to a longitudinal groove 226 that extends from the detents 225 towards the end of the second portion 221 nearest to the first portion 211, to provide tracks on which the latches of the post 230 can travel when the post 230 is advanced distally. Alternatively, the entire outer surface of the region of the second portion 221 between the detents 225 and the end of the second portion 221 nearest to the first portion 221 can have a reduced diameter compared to other regions of the second portion 221.

Figures 14A, 14B:
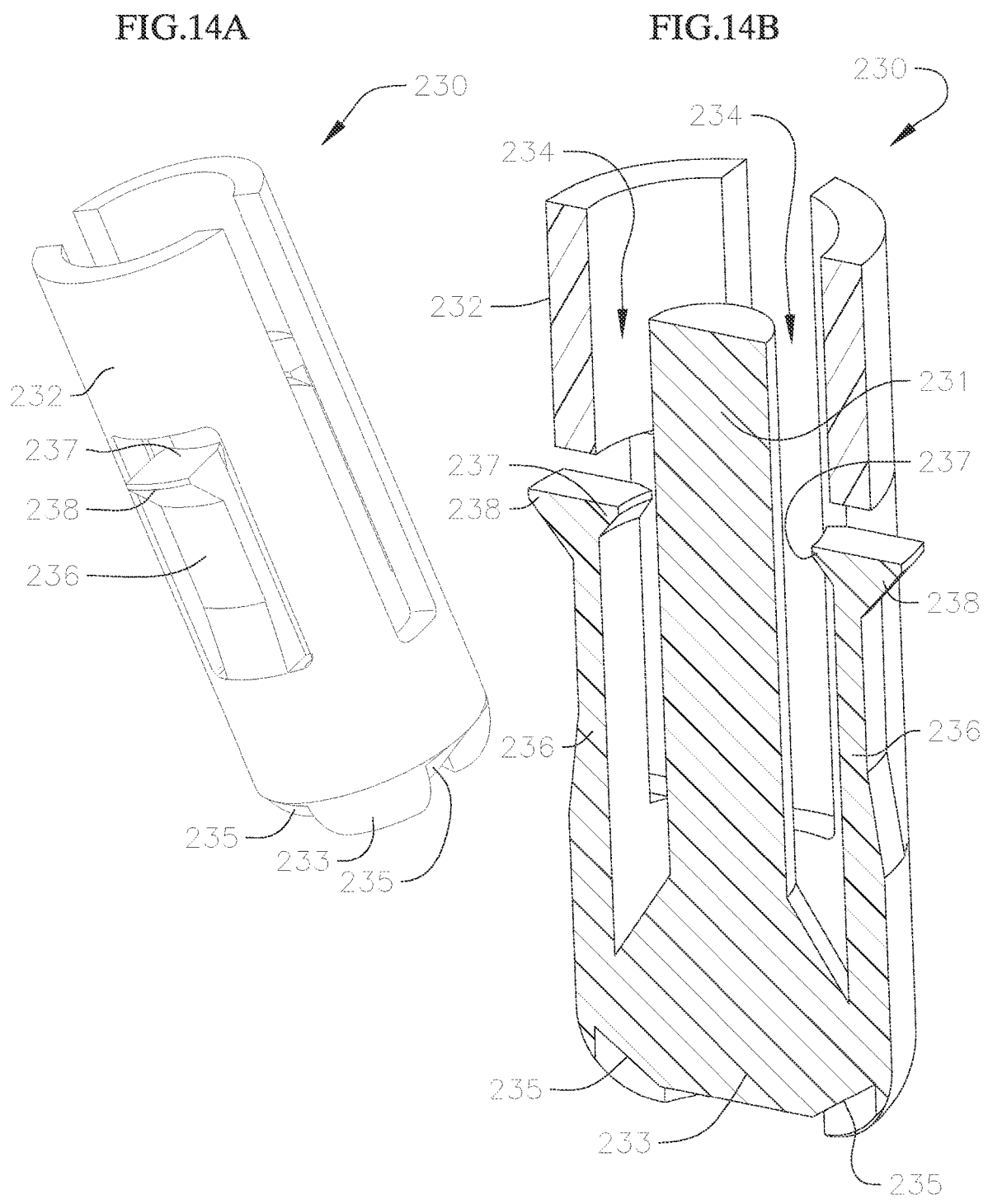
FIGS. 14A and 14B respectively show a perspective view and a cross-sectional view of a post of the valve holder of FIGS. 11 and 12.

The post 230 is shown in greater detail in FIGS. 14A and 14B. The post 230 is of a longitudinal construction, and includes two main longitudinally extending sections, a solid rod-shaped central body 231 and a tubular section 232 that surrounds the central body 231. The central body 231 and the tubular section 232 are attached at only one end 233 (i.e., a distal end) of the post 230, while the opposite end of the central body 231 and the tubular section 232 remain free, forming a cylindrically-shaped recess 234 extending between the central body 231 and the tubular section 232 for a majority of the post 230. The cylindrically-shaped recess 234 provides a space into which the second portion 221 of the hub 210 can extend. In the illustrated embodiment, the tubular section 232 is also slightly longer axially than the central body 231, but in other embodiments, the lengths may be similar, or the central body 231 may be longer than the tubular section 232.

The central body 231 forms a plunger region of the post 230 that is configured to extend into the second portion 221 of the hub 210. A width of the rod-shaped central body 231 is smaller than inner diameters of both the first and second regions 223, 224 of the bore 222 of the hub 210, while a length of the central body 231 is such that it can extend through the first region 223 of the bore 222, and in some embodiments, at least partially into the second region 224 of the bore 222. Additionally, a free end of the central body 231 forms a flat or other suitable surface against which another component (e.g., a distal end of an extension handle) can abut. Meanwhile, the size of the cylindrically-shaped recess 234 is such that the second portion 221 of the hub 210 can easily extend therethrough as well. In this manner, the post 230 can be attached from a distal end of the hub 210 (i.e., from an end of the hub 210 where the first portion 211 is located), so that the second portion 221 of the hub 210 is sandwiched between the central body 231 and the tubular section 232 of the post 230.

The distal end 233 of the post 230 securely attaches the tubular section 232 to the central body 231. In addition, an outer surface of the post 230 at the distal end 233 may have a tapered or curved profile, and may further be arranged with a plurality of grooves 235 that meet at a center of the outer surface of the distal end 233 and extend radially outwards therefrom. A number of grooves 235 will generally correspond to a number of radial projections 213 on the hub 210, and will align with and extend towards the radial projections 213 when the post 230 is attached to the hub 210. Therefore, the number of grooves 235 also corresponds to a number of commissure posts on the prosthetic valve intended to be attached to the valve holder 200. In other embodiments, other engagement features other than grooves that are capable of securely engaging sutures that run over the distal end 233 of the post 230 can be used instead.

The post 230 also includes one or more extensions 236 that extend from the distal end 233 toward the opposite end of the post 230. The embodiment shown includes two extensions 236 located across from one another, and that correspond to the positions of the detents 225 on the hub 210. The extensions 236 may be positioned radially from a central axis of the post 230 at about a same distance as the tubular section 232, and may be surrounded by other portions of the tubular section 232 on three sides. In some embodiments, the extensions 236 may be formed, for example, by etching or forming grooves in the tubular section 232. The extensions 236 are flexible, and can be elastically urged or flexed radially inwardly and/or outwardly. At free ends of the extensions 236, one or more latching features can be constructed or formed. A first latching feature 237 on each extension 236 extends inwardly and is sized and shaped to engage the detents 225 on the hub 210, to stop proximal movement of the post 230 relative to the hub 210 when the components are connected to one another. A second latching feature 238 can also be formed at the free end of each extension 236, and can be a radially outwardly extending projection, or can simply be formed by a flat end face of each of the extensions 236 that extends perpendicularly to the central axis of the post 230.

Figure 15A:
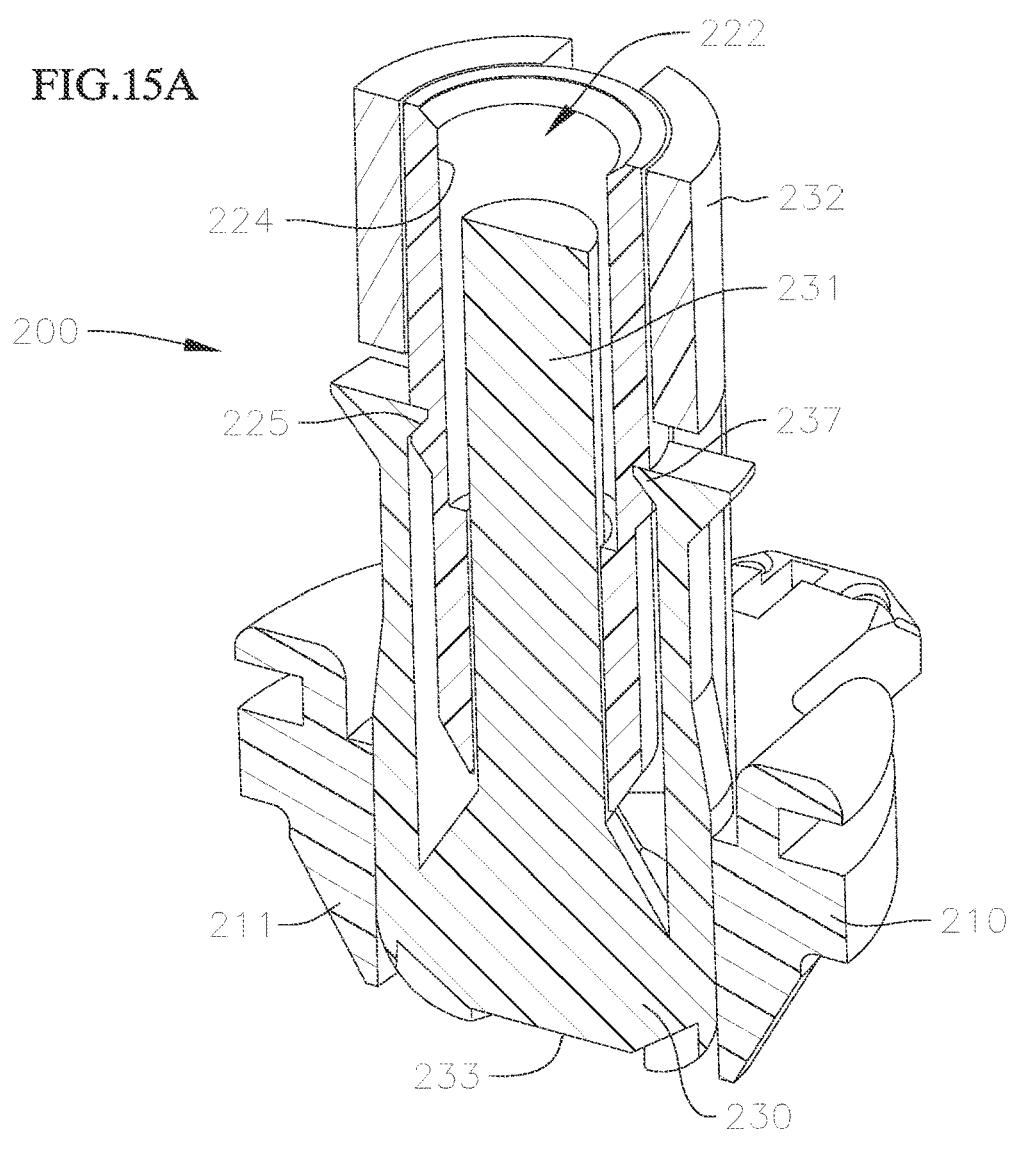
FIG. 15A shows a perspective view with a cross-section of the valve holder of FIGS. 11 and 12 in a first, undeployed, configuration.

FIG. 15A shows a perspective view of the assembled valve holder 200 with a cross-section showing interactions between the various parts or components. The valve holder 200 in FIG. 15A is in a first, un-deployed, configuration, where the valve holder 200 has not yet been attached to a separate extension handle that can be used to help maneuver the valve holder 200 and an attached prosthetic valve to the implant site.

As can be seen in FIG. 15A, the post 230 has been attached to the hub 210, where the tubular section 232 of the post 230 extends through the gaps 218 of hub 210, while the central body 231 extends through the bore 222 of hub 210. Here, the first latching features 237 latch in the detents 225, to prevent further proximal movement of the post 230 relative to the hub 210. This latching also temporarily holds the post 230 at the un-deployed configuration and also restricts distal motion relative to the hub 210, so that the valve holder 200 can be held in the un-deployed position, for example, during manufacturing, shipping, unpacking, prior to being attached to a prosthetic valve, etc. This hold can be overcome by a distal pressure on the post 230, as will be discussed in greater detail below. In this position, the distal end 233 of the post substantially aligns with, or generally does not protrude or only protrudes marginally from, a distal end of the first portion 211 of the hub 210, which also represents a distal end of the entire hub 210. In addition, the respective proximal ends of the hub 210 and the post 230, may also be substantially aligned. Meanwhile, central body 231 of the post 230 extends entirely through the first region 223 of the bore 222 of the hub 210 and may also extend at least partially into the second region 224 of the bore 222.

Figure 15B:
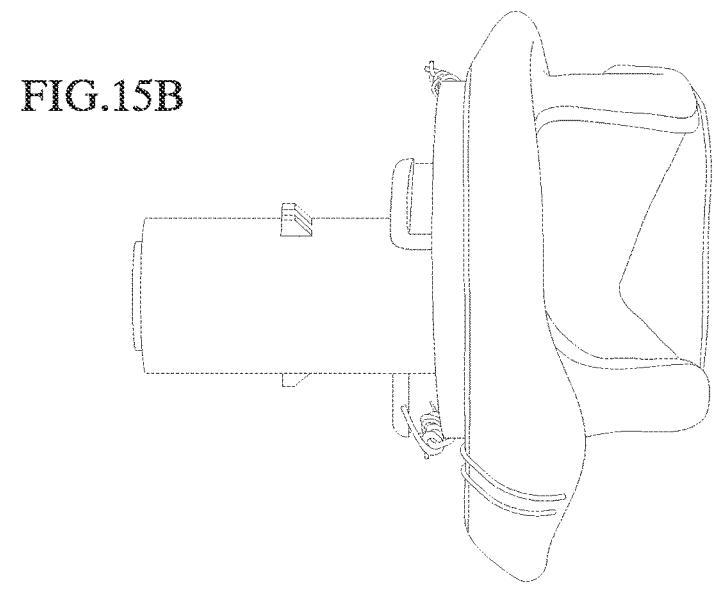
FIG. 15B is an image showing the valve holder in the first configuration with a replacement valve attached thereto.

FIG. 15B provides an image showing the valve holder 200 in the first, un-deployed position and attached to a prosthetic valve via a series of sutures or other flexible material or attachment mechanism. The valve holder 200 connects to, and may extend partially into, an inflow side of the prosthetic valve, while the radial projections 213 on the hub 210 provide a surface on which the prosthetic valve rests and limit how far the valve holder 200 can be advanced therein. The connection sutures are looped or otherwise connected through the apertures 214 on the projections 213, and extend through the sewing ring or other portion of the base of the valve stent and then over or through the tips of the commissure posts of the prosthetic valve. The sutures are then extended radially inward from the ends of the commissure posts over the outflow end of the prosthetic valve to a central flow axis of the prosthetic valve. The sutures are then criss-crossed, interwoven, or otherwise engage with one another at the central flow axis, so that the segments of sutures converge or cross at the central flow axis, spaced apart axially from the leaflets and other portions of the prosthetic valve. This convergence point or crossing region provides an area at which the distal end 233 of the post 230 can contact all of the suture segments simultaneously, in order to shift or move the suture segments, and to consequently control the positioning or orientation of the commissure posts respectively connected to each of the suture segments.

Figures 16A, 16B:
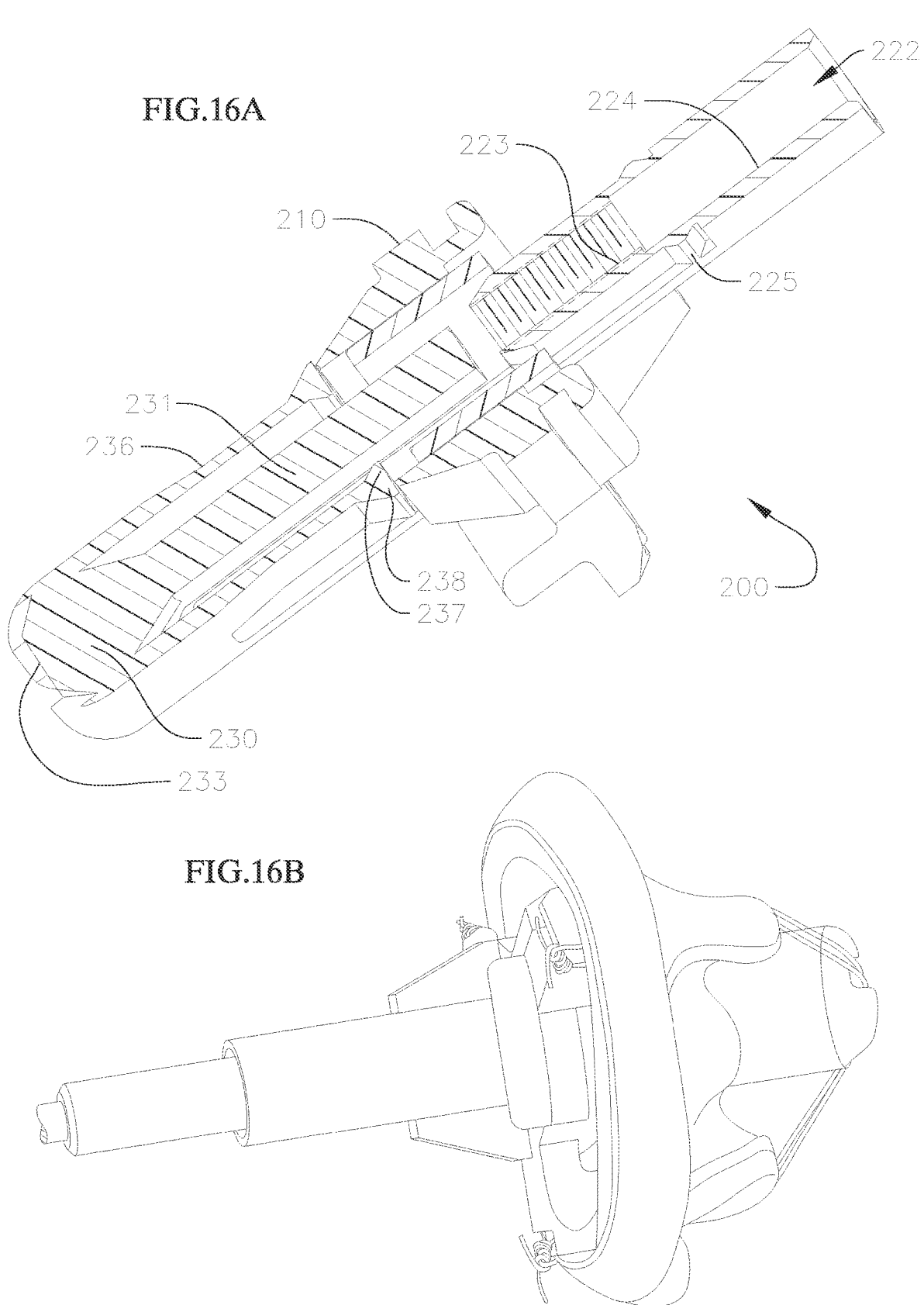
FIG. 16A shows a perspective view with a cross-section of the valve holder of FIGS. 11 and 12 in a second, deployed, configuration.
FIG. 16B is an image showing the valve holder in the second configuration with a replacement valve attached thereto.

FIG. 16A shows a perspective view of the valve holder 200 with a cross-section showing the interactions between the various parts. The valve holder 200 in FIG. 16A has been moved from the un-deployed configuration shown in FIG. 15A to a second, deployed configuration, where the post 230 has been pushed or urged axially in a distal direction relative to the hub 210, so that when the valve holder 200 is in the deployed position, the post 230 extends distally from the distal end of the hub 210 by a significant amount, for example, by more than half of the axial length of the post 230 as illustrated in FIG. 16A. In other embodiments, the post 230 can extend more or less than in the illustrated embodiment when in the deployed position, depending for example on the size of the prosthetic valve and/or the amount of deflection of the commissure posts that is desired. The displacement of the post 230 relative to the hub 210 can be effected by an external distal force that is applied to the post 230. This force can be applied to the free end of the central body or plunger 231 of the post 230, for example, by a separate extension handle (not shown) to which the valve holder 200 can be connected. Such handles are already readily used by practitioners to help maneuver existing prosthetic valve and valve holder assemblies to implant sites.

A distal end of such an extension handle can be inserted through a proximal end of the bore 222 of the hub 210 to contact the central body 231 of the post 230. Here, the distal end of the handle is threaded with threads corresponding to the threads on the first region 223 of the bore 222, while as discussed earlier, the second region 224 of the bore 222 is unthreaded and is wider than the first region 223 of the bore 222. Therefore, even if the proximal end of the handle is not exactly aligned with the bore 222 during initial insertion, the second region 224 acts as an integrated guide on the valve holder 200 that facilitates easier guiding and more precise alignment of the proximal end of the handle with the bore 222. The second region 224 can also act as a thread guide, so that the respective threads of the proximal end of the handle and the first region 223 of the bore 230 will be aligned when they eventually engage, thereby preventing potential occurrences of cross-threading, as well as avoiding damage to the threaded surfaces and/or for example, creation of loose plastic fragments or particles.

The distal end or tip of the handle also provides an abutting surface, such that linear or axial advancement or displacement of the handle through the bore 222 will push the central body 231 of the post 230 distally relative to the hub 210, so that the distal end 233 of the post 230 extends distally past the distal end of the hub 210, as previously discussed. An end user can apply an increasing axial force or pressure on the central body 231 of the post 230 with the handle until the pressure overcomes the retention force between the latches 237 and the detents 225. In this manner, the latches 237 can be dislodged or disengaged from detents 225, for example, by deflecting the extensions 236 outwards and advancing the first latches 237 over distal ridges of the detents 225. Thereafter, the post 230 can be displaced further distally relative to the hub 210, until the threaded handle reaches and engages the threaded first region 223 of the bore 222. Then, the handle can be threaded into the first region 223 to fully connect the handle to the valve holder 200 and to displace the post 230 further to its final deployed position.

In some embodiments, for example, as can be seen in FIGS. 15A and 16A, an inner wall of the hub 210 causes a slight inward deflection of the extensions 236 during further distal displacement of the post 230. Then, upon sufficient displacement of post 230, the extensions 236 will pass this inner wall in the distal direction and will expand slightly radially outwardly, and the second latching features 238 on extensions 236 will engage a corresponding surface or abutting feature on hub 210, to hold the valve holder 200 in the deployed configuration. In the embodiment disclosed, the distal end of the hub 210 forms this abutting surface, but in other embodiments, the abutting surface can instead be, for example, an internal surface of the hub 210.

FIG. 16B is an image showing the valve holder 200 connected to a prosthetic valve and actuated by an extension handle that is connected to the second portion 221 of hub 210, and where the valve holder 200 is held in the second, deployed configuration. As discussed above, in the deployed configuration, the distal end 233 of the post 230 extends distally from the distal end of the hub 210. When the valve holder 200 is attached to the prosthetic valve and in the deployed configuration, as shown, the post 230 displaces the valve leaflets and extends through the outflow end of the valve. The distal end 233 of the post 230 engages the sutures at the suture crossing region that is aligned with the central flow axis of the valve, as previously described, and pushes or displaces the crossing region of the sutures distally away from the prosthetic valve. The axial forces resulting from the torque applied to the connected handle when the handle is screwed into the bore 222 of the hub 210 and pushes against the central body 231 of post 230 can overcome the tension on the sutures in order to displace the sutures. This displacement of the suture crossing region by the post 230 results in the sutures forming a tent-like or umbrella configuration extending distally from the prosthetic valve. The tension from the axial displacement of the sutures, in turn, pulls or deflects the commissure posts of the prosthetic valve inward as well.

Once the valve holder 200 has been adjusted to the deployed configuration with the prosthetic valve attached, as described above, the practitioner can then use the attached handle to maneuver the valve holder 200 and prosthetic valve to the implant site, and can further attach the prosthetic valve to the native valve annulus, for example, by tying or otherwise applying suture knots between the sewing ring and the native annulus. During the advancement of the prosthetic valve to the implant site, the commissure posts are deflected inwardly, so that occurrences of suture looping or other entanglement of sutures with the commissure posts are reduced or eliminated.

Furthermore, the sutures themselves also form additional angled surfaces that slope outwardly from the central posts to the commissure posts when they are arranged in the tent-like state while in the deployed configuration. The angled sutures also serve to deflect any other sutures or obstructions that the prosthetic valve might engage or encounter away from the valve during advancement to or attachment at the implant site. Together, each of the angled sutures and corresponding angled commissure posts form a continuous track that can radially deflect most, if not all, obstructions away from the assembly. This arrangement effectively prevents entanglement or other damage to the prosthetic valve during implantation, even for procedures where the prosthetic valve is advanced to the native valve annulus from the inflow side of the native valve, and where the commissure posts of the prosthetic valve are pointed distally during advancement and are obstructed or blocked from the view of the surgeon or practitioner.

After the prosthetic valve has been securely attached at the implant site, the sutures attaching the valve holder 200 to the prosthetic valve can be untied or cut, to release the valve from the valve holder 200 and to allow the prosthetic valve to return to its original shape. The valve holder 200 can then be removed from the implant site and the fully implanted valve.

In the embodiment described, actuation of the valve holder 200 is simplified, since adjustment of the valve holder 200 to the deployed configuration involves only attachment of the handle, which is a step that is already performed by the practitioner when implanting existing prosthetic valves, and since a same number of turns needed to fully connect the handle will also automatically actuate or deploy the valve holder 200. Therefore, the practitioner does not need to learn or perform any additional steps to properly deploy and use the valve holder 200, thereby reducing the possibility of user error.

Meanwhile, unlike the valve holder 100 discussed above with respect to FIGS. 3 to 10B, the valve holder 200 only utilizes the distal motion of the post 230 relative to the hub 210 to adjust the valve holder 200 to the deployed position (without, for example, movement of any arms, etc.), and therefore does not include any additional sutures between respective components of the valve holder 200. Therefore, some embodiments of the valve holder 200 may only include two parts, while the only sutures used with the valve holder 200 are those that connect the valve holder 200 to the prosthetic valve and that effect the positioning or distraction of the commissure posts of the valve. Additional sutures may still be incorporated in alternative embodiments, for example, for detaching the second portion 221 of the hub 210 from the rest of the valve holder 200, as will be discussed in greater detail below. In any case, the valve holder 200 can be constructed to be similar in size to currently existing valve holders, and since the valve holder 200 has a reduced number of parts, and since the design and construction are kept simple, manufacturing costs can also be kept low, for example, comparable to that of currently existing valve holders.

In different embodiments, the handle may be detached from the valve and valve holder assembly at different points during the valve implantation process. For example, in embodiments where the valve holder does not include a second latching feature 238, the handle may have to remain attached to the valve holder 200 until it is desired for the prosthetic valve to return to its original configuration, e.g., after the prosthetic valve has been fully implanted at the implant site. In other embodiments, where for example the second latching feature 238 is incorporated, the handle can be detached right after, or even before, final advancement of the prosthetic valve to the implant site, to provide additional space for the practitioner to apply additional suture knots and/or other connections during final attachment of the prosthetic valve to the native annulus, since the second latching feature 238 allows for the valve holder 200 to be held at the deployed configuration even if the handle is detached.

Figures 17, 18, 19:
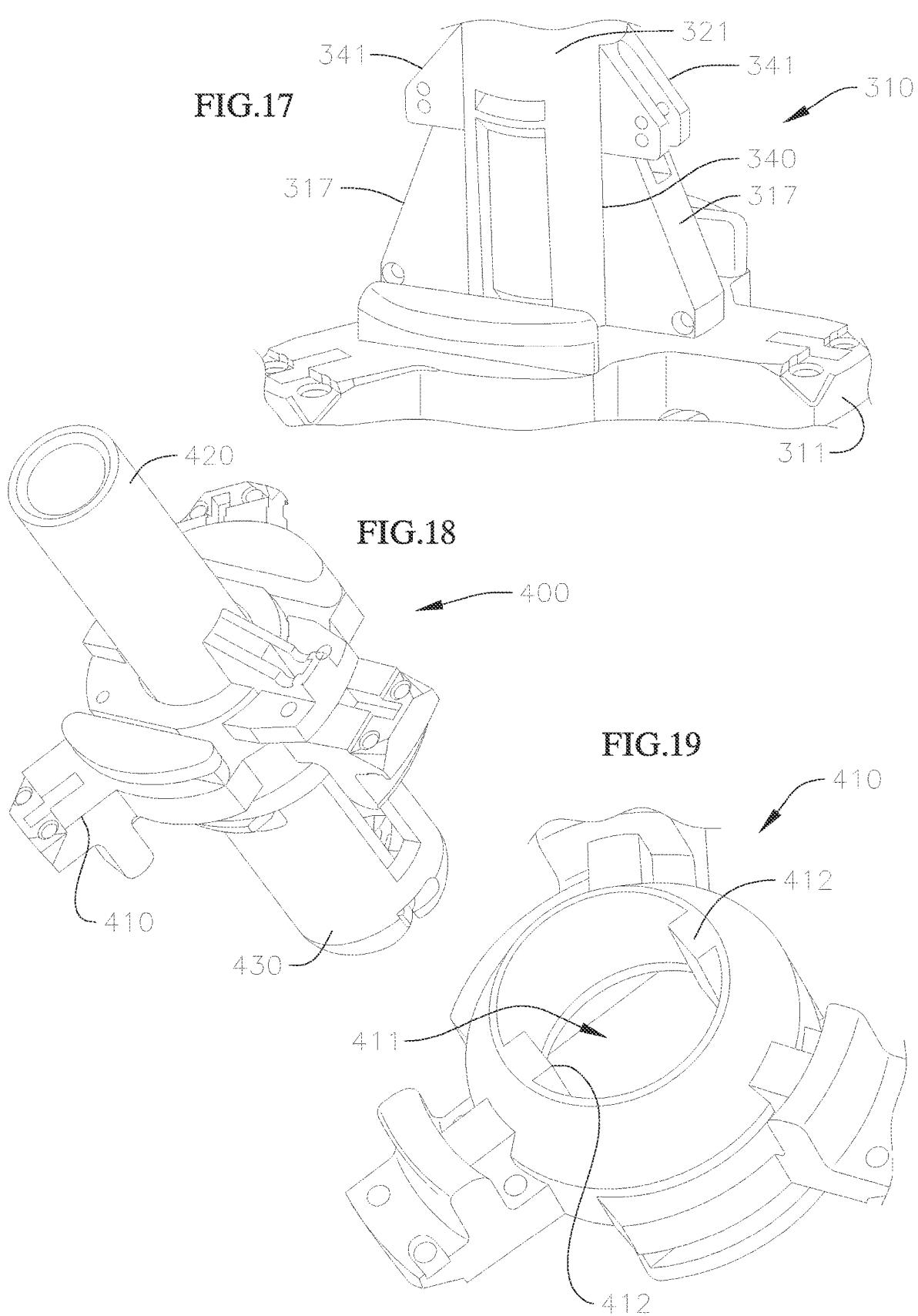
FIG. 17 shows a perspective view of a portion of a valve holder for a prosthetic mitral valve according to a modified embodiment, where the valve holder has a hub with a separable adapter portion.
FIG. 18 shows a perspective view of a valve holder for a prosthetic mitral valve according to a second modified embodiment with a separable adapter portion.
FIG. 19 shows a perspective view of a portion of the hub of the valve holder of FIG. 18.

To further accommodate easier removal of the handle from the valve holder assembly, the hub of the valve holder can in some embodiments be constructed as two separable pieces. FIG. 17 shows a perspective view of a portion of a valve holder for a prosthetic valve according to a modified embodiment, where the valve holder has a hub with a separable adapter portion. A hub 310 of a modified valve holder includes a main hub body 311 and an adapter or insert 321. The adapter 321 can be constructed similarly to all or part of the second portion 221 of the valve holder 200 discussed above, where the adapter 321 also has a through bore with a threaded first region. Other embodiments of the adapter 321 may be constructed differently and have different parts or portions, but will generally house the threaded region where the handle attaches to the valve holder, so that the threaded region is removable from the rest of the valve holder.

The adapter 321 is designed to easily mate with and detach from the main hub body 311. For example, the main hub body 311 can include one or more vertical struts or supports 317 similar to the supports 217 on the hub 210 discussed above. A distal end of the adapter 321, meanwhile, may be constructed with cutouts 340 into which the supports 317 can extend. In both embodiments with or without supports 317 and cutouts 340, other abutting surfaces or interlocking features (not shown) may also be integrated into the main hub body 311 and/or the adapter 321, to facilitate attachment between the pieces and to define a held or assembled position therebetween.

In addition, the adapter 321 can include one or more apertures or other features for attaching sutures. For example, in the embodiment shown in FIG. 17, the adapter 321 includes two pairs of projections 341 with apertures. The projections 341 are positioned circumferentially opposite to one another on an outer surface of the adapter 321. A pair of corresponding apertures are located near a base of each of the supports 317 on the main hub body 311. These apertures can be used to tie connection sutures on either side of the adapter 321 to the main hub body 311 to securely hold the respective components together. When the connection sutures are untied or cut, the adapter 321 can then be easily removed or detached from the main hub body 311. In other embodiments, the apertures or other suture attachment features may be located on other parts of the adapter 321 and/or the main hub body 311.

Embodiments with a removable adapter 321 as described above will also include a second latching feature similar to the one described above with reference to the valve holder 200 in FIGS. 11 to 16B, which holds the valve holder in the deployed position once it has been fully actuated. When the handle is connected to this modified valve holder and the valve holder is held in the deployed position, the handle only directly contacts the adapter 321 of the hub 310 (while the distal end or tip of the handle may also still be abutting the central body or plunger of the post). Therefore, when it becomes desirable to remove the handle, for example, after the handle has been used to maneuver the prosthetic valve and valve holder assembly to the implant site, and before the suture knots have been applied for final attachment of the prosthetic valve, the connection sutures between the adapter 321 and the main hub body 311 can be severed, and the handle can be removed together with the adapter 321. Removal of the handle and adapter 321 may be advantageous, for example, to provide even more space for the surgeon to finally adjust and/or attach the prosthetic valve at the implant site. In addition, utilizing a separate removable adapter 321 in the manner described above simplifies the removal process to only involving the cutting of sutures. This also eliminates the need to manually unthread or unscrew the handle from the valve holder, which may be cumbersome or difficult, due for example, to space constraints in the operating room.

FIGS. 18 to 22B show various views of another modified embodiment of a valve holder with a separable adapter portion. Descriptions of parts and features that are the same or similar to those in previously described embodiments will not be repeated.

FIG. 18 shows a perspective view of a valve holder 400, with a hub or holder portion 410, an adapter 420, and a post 430. Similar to the embodiment described with respect to FIG. 17, the adapter 420 in this embodiment is detachable from the hub 410. However, unlike the main hub body 311 in FIG. 17 which includes the supports 317, the hub 410 does not have any tall vertical struts or supports that extend proximally from the rest of the hub 410. During an implantation procedure, after the adapter 420 (and the connected holder) have been detached, additional annular sutures may still have to be applied and knotted to firmly secure the prosthetic valve to the native valve annulus. While removal of the adapter 420 and handle provides additional space for the surgeon to apply and tie these additional sutures, any other projections or protrusions present can still form obstacles that can cause tangling or catching when the annular sutures are being tied down, and may lead to undesirable air knots that may compromise the connection and/or function of the prosthetic valve. On the main hub body 311 in FIG. 17, the most prominent of these possible obstructions are the supports 317.

Therefore, the hub 410 is designed without any such exterior struts or supports, in an effort to make the proximal face of the hub 410 flatter, to reduce the profile of the hub 410, and to also reduce the possibility of any of the sutures tangling or getting caught on the hub 410, or of air knots, when the prosthetic valve is tied down at the implant site.

Meanwhile, while the supports in the previous embodiments may have also served to support and/or guide the movement of the post relative to the hub, other features can be added to the hub 410 and/or adapter 420 to replace the functionality of the supports. For example, as can be seen in FIG. 19, projections or supports 412 can instead be formed on an inner wall of an inner cavity 411 of the hub 410. In the embodiment shown, the inner cavity 411 provides sufficient space through which the post 430 can move or translate axially. Meanwhile, the supports 412 are formed as flat longitudinal projections that extend over the length of the inner cavity 411. Two projections 412 arranged opposite to one another are shown in FIG. 19, but other embodiments may only have one such support, or may have more than two supports, and the supports may have any other shape, size, and/or length to help facilitate stability and alignment of the post 430 when the post 430 is held in and moves through the inner cavity 411 of the hub 410.

Figure 20A:
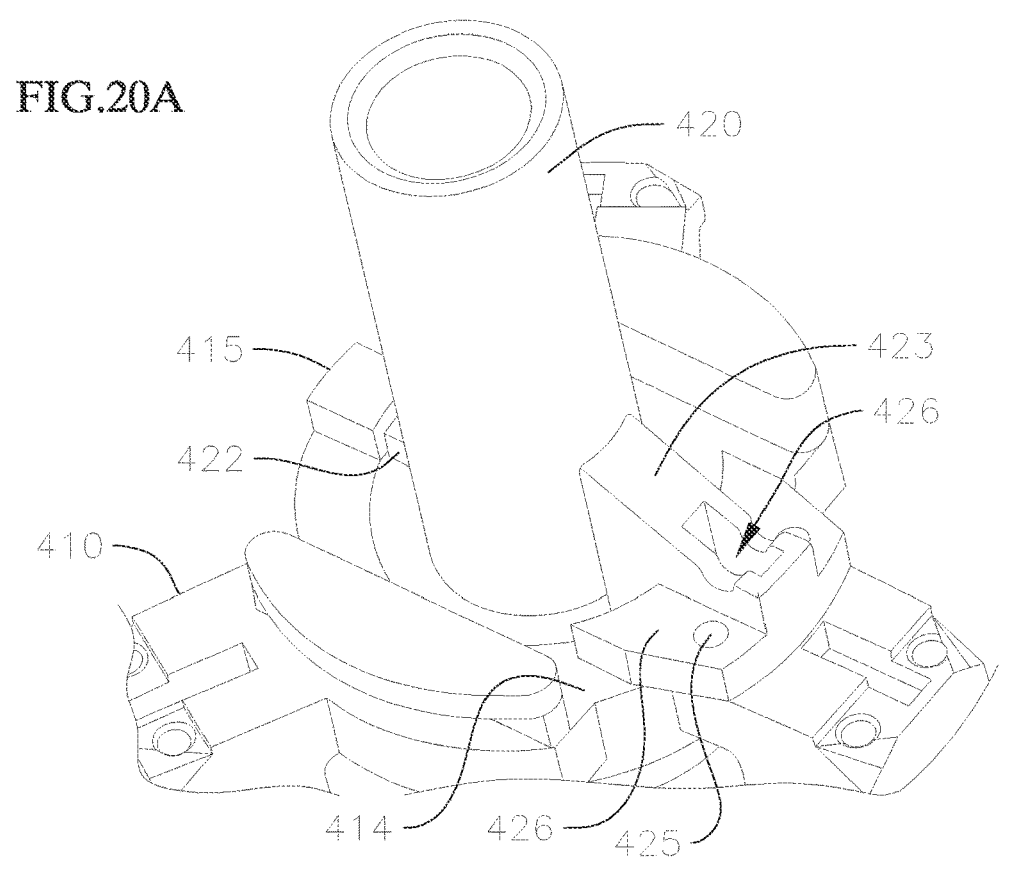
FIGS. 20A and 20B respectively show a perspective view and a cross-sectional view of a portion of the valve holder of FIG. 18.
Figure 20B:
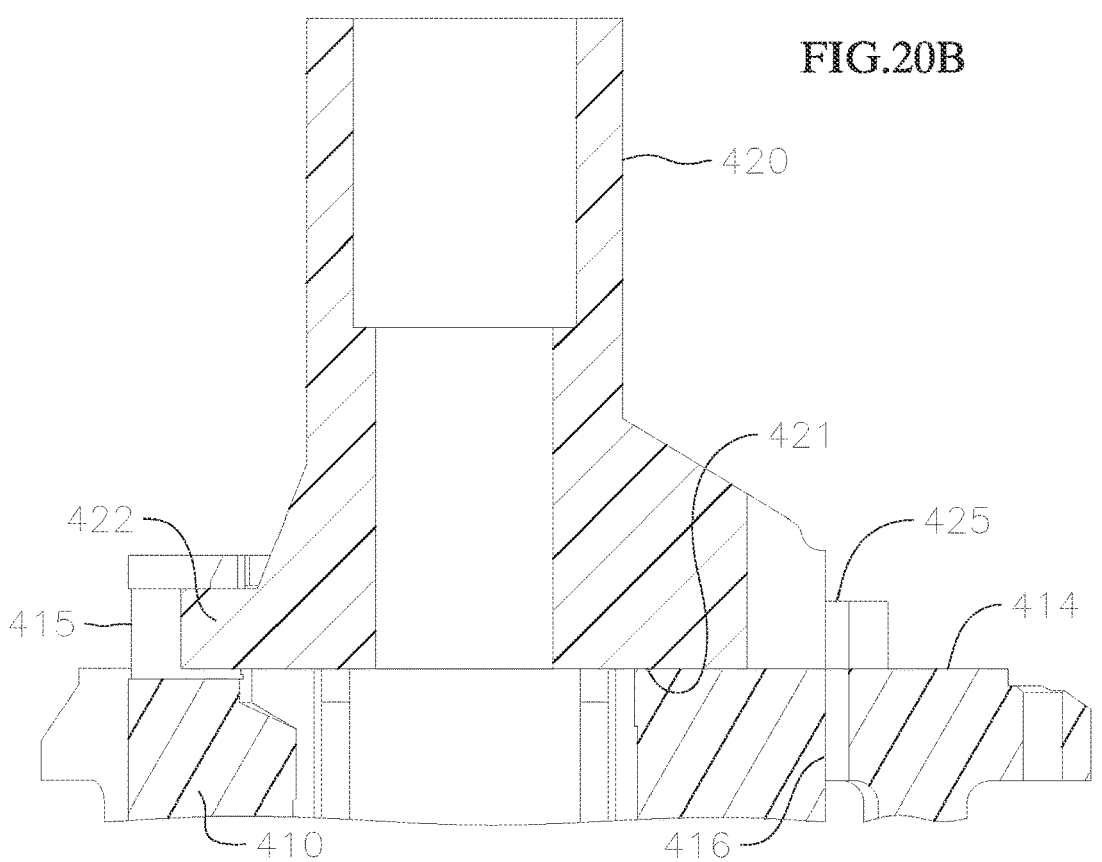

Additional changes can also be made to facilitate easier detachment of the adapter 420 from the hub 410. FIGS. 20A and 20B show an additional feature of the modified valve holder 400 of FIG. 18, for simplifying the detachment of the adapter 420 from the hub 410. Referring back first to the valve holder in FIG. 17, the adapter 321 is attached to the main hub body 311 via sutures that connect to the two supports 317. Therefore, two suture connections are used to attach the adapter 321 to the main hub body 311 in that valve holder embodiment, and detachment of the adapter 321 from the main hub body 311 involves cutting both of the suture connections.

The design of the valve holder 400 instead allows for a secure connection of the adapter 420 to the hub 410 via a single suture connection, such that removal of the adapter 420 from the hub 410 requires cutting only that single suture connection, thereby providing for a quicker and easier detachment process.

Absent any of the tall supports or struts found in earlier described embodiments, the central region 414 of the proximal end of the hub 410 is substantially flat, and a corresponding distal end surface 421 of the adapter 420 can also be made substantially flat, so that the respective ends can rest and slide easily against one another. The proximal end of the hub 410 further has an interlock feature 415 on one side. The interlock feature 415 can be, for example, a projection with a groove or a cutout oriented radially inwards towards a central axis of the hub 410, or can be any other shape, such as a hook or latch, that can facilitate engagement of the adapter 420 on one side of the inner cavity 411. On a side of the inner cavity 411 circumferentially opposite to the interlock feature 415, an aperture or other engagement feature 416 can be incorporated into the hub 410. In the embodiment shown, the engagement feature 416 is formed as one or more through bores that extend axially through the hub 410.

Meanwhile, a complementary interlock feature 422 is formed on the adapter 420 to engage the interlock feature 415 on the hub 410. In the embodiment shown, the interlock feature 422 is formed as a radial projection at the distal end surface 421 of the adapter 420 that is sized and shaped to fit into the groove in the interlock feature 415 on the hub 410. The respective flat surfaces on the hub 410 and the adapter 420 allows for easy sliding engagement between the respective interlock features 415, 422 when the adapter 420 is being attached to the hub 410, as well as easy sliding disengagement when the adapter 420 is detached from the hub 410.

On a side opposite the interlock feature 422, the adapter 420 has another projection 423 that projects radially outwardly from the tubular body of the adapter 420. The projection 423 is relatively narrow in width, and connects to a relatively wider foot region 424 that is positioned further radially outwardly. An aperture or other engagement feature 425 is formed on either the projection 423 or the foot region 424, at a position corresponding to the engagement feature 416 on the hub 410 when the interlock features 415, 422 are engaged. In this embodiment, the engagement feature 425 is formed as one or more through bores that align with the through bores 416 on the hub 410. The through bores 416, 425 collectively form one or more channels that can be used for the suture tie down which connects the adapter 420 to the hub 410. As can best be seen in FIG. 20A, an additional projection and/or recess 426 can be formed on the adapter 420 over which the suture connection extends. The recess 426 can provide an easy access point at which the suture connection can be cut when removal of the adapter 420 is desired.

When the adapter 420 is connected to the hub 410, the tubular body of the adapter 420 is aligned along the central axis of the hub 410, and is positioned coaxially with the inner cavity 411. A width or diameter of the tubular body of the adapter 420 is smaller than a width or diameter of the inner cavity 411, such that a circumferential gap is formed between the hub 410 and the adapter 420. In this manner, the tubular portion of the post 430 can extend through the gap and over the tubular body of the adapter 420. In this position, the interlock feature 422, formed as the projection, extends across the gap to connect the adapter 420 to the hub 410 on one side, while the projection 423 extends across the gap to connect the adapter 420 to the hub 410 on the opposite side. The positioning of the wider foot region 424 away from the tubular body of the adapter 420 exposes a narrower portion of the projection 423 therebetween, so that the width of the projection 423 that covers or extends over the gap can be minimized to allow additional space for the post 430 to move. Meanwhile, the wider foot region 424 forms a planar connection over an increased surface area between the hub 410 and the adapter 420, to provide for a more stable or secure connection between the respective parts.

As discussed above, removal or detachment of the adapter 420 from the hub 410 with this design involves only a single suture cut, for example, at the recess 426, and then sliding of the projection 422 out of the groove 415. The design features of the respective components also provide for a secure connection between the parts prior to removal of the adapter 420.

Figure 21A:
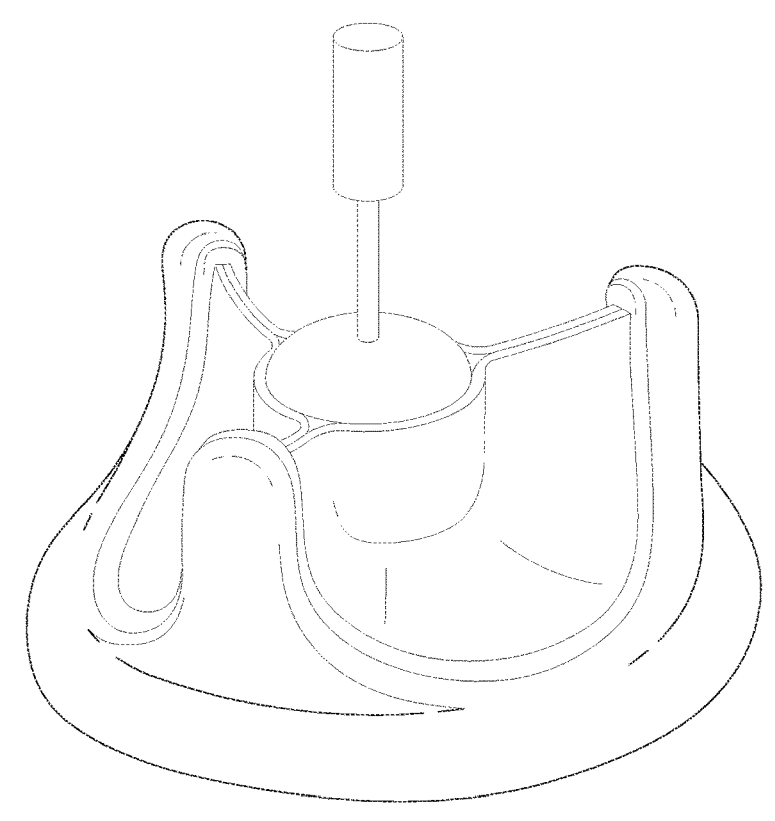
FIG. 21A is an image showing a valve holder and a valve interacting with a separate fixture post and a metal pin during attachment of the valve to the valve holder.

Meanwhile, a current technique for sewing or otherwise connecting a valve to a valve holder prior to implantation involves connecting the prosthetic valve to a distal end of the valve holder while a separate fixture post and a metal pin that is supported by the fixture post is positioned on or through the hub of the valve holder. An example of such a fixture post and metal pin assembly interacting with a valve holder and a prosthetic valve is shown in FIG. 21A. When the prosthetic valve is placed on the distal end of the valve holder, the metal pin, and in some cases part of the fixture post, will extend distally through the outflow end of the valve. The prosthetic valve is then connected to the distal end of the valve holder, and the metal pin provides a tool or access point around which the sutures that run over the outflow end of the prosthetic valve can be criss-crossed or interwoven to form the suture crossing region that the post will deflect when the valve holder is in the deployed configuration. However, the valve holder 200 described with reference to FIGS. 11 to 16B is assembled by also inserting the post 230 from the distal end of the hub 210. Therefore, the post 230 must be assembled to the hub 210 prior to attachment of the prosthetic valve, since if the valve is attached to the hub 210 first, then the attached prosthetic valve would block and prevent the insertion of the post 230. However, if the post 230 is attached to the valve first, then the post 230 will interfere with the attachment of the fixture post and/or the metal pin that are used to facilitate attachment of the prosthetic valve. As such, it may be difficult or impossible to attach a prosthetic valve to the valve holder 200 using the above technique.

Figure 21B:
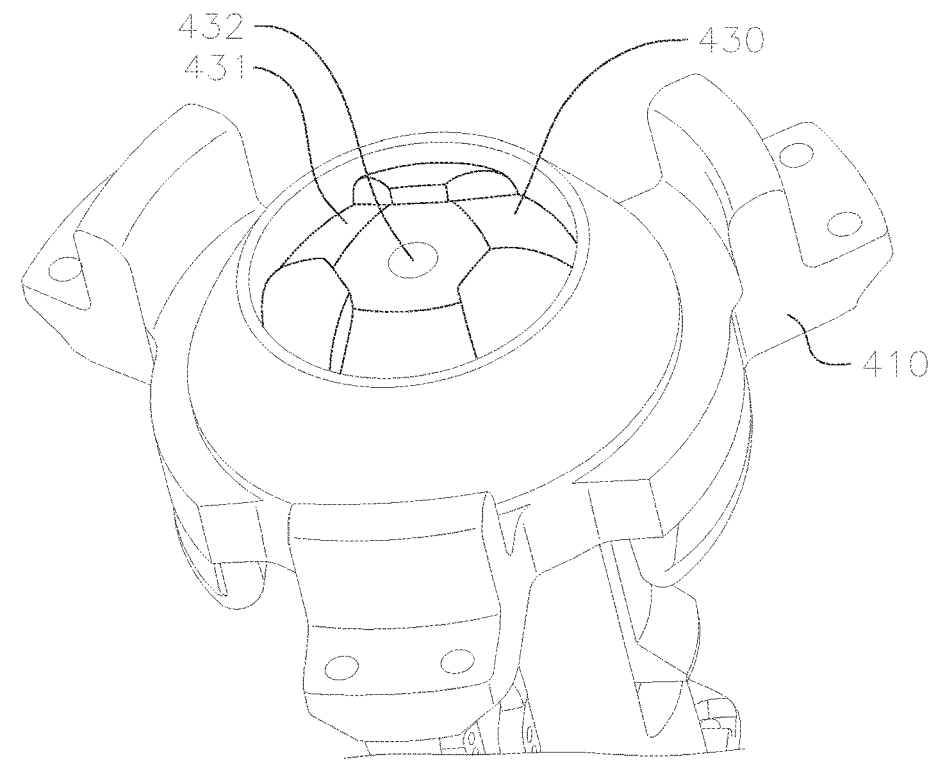
FIG. 21B shows a perspective view of a portion of the modified valve holder of FIG. 18 configured to hold the metal pin.

FIG. 21B is a perspective view of the distal end of the valve holder of FIG. 18, where the post 430 has been modified to hold the metal pin described above for attaching the prosthetic valve to the valve holder. As can be seen in FIG. 21B, the distal end of the post 430 has grooves 431 that are used to engage the sutures that run over the prosthetic valve at the crossing region, which can be similar to the grooves formed on the posts of other valve holders described in earlier embodiments. In addition, a separate axially extending hole 432 is also formed at the distal end of the post 430. The hole 432 is positioned along at central axis of the post 430, and is sized to receive and to securely hold the metal pin described above during attachment of a prosthetic valve to the valve holder 400. Therefore, the post 430 can be assembled to the hub 410 prior to attaching the prosthetic valve to the valve holder 400, and the metal pin can then be inserted into the hole 432 on the post 430 to facilitate attachment of the valve. In this manner, the prosthetic valve can be attached to the valve holder 400 using a similar technique to the existing technique described above, while eliminating the need for a separate fixture post.

Another potential issue that can arise with the valve holder 200 in FIGS. 11 to 16B is that, while the second latching feature between the respective parts holds the valve holder 200 in the deployed configuration and generally prevents proximal movement of the post 230 relative to the hub 210, the second latching feature does not further prevent distal movement of the post 230 relative to the hub 210. Distal movement of the post 230 is instead prevented by the suture crossing region at the outflow end of the prosthetic valve pushing against the distal end of the post 230. However, after the prosthetic valve is implanted, and the valve holder 200 is disconnected from the prosthetic valve and removed from the implant site, for example, by cutting the sutures connecting the valve to the valve holder 200, the pressure applied by the sutures on the distal end of the post 230 is also released, and there is no longer any force preventing the post 230 from falling out of or otherwise detaching distally from the hub 210. In this case, the post 230 can inadvertently damage the implanted valve when the components detach, or in a worst case scenario, the post 230 may be inadvertently left behind at the implant site.

Figures 22A, 22B, 23:
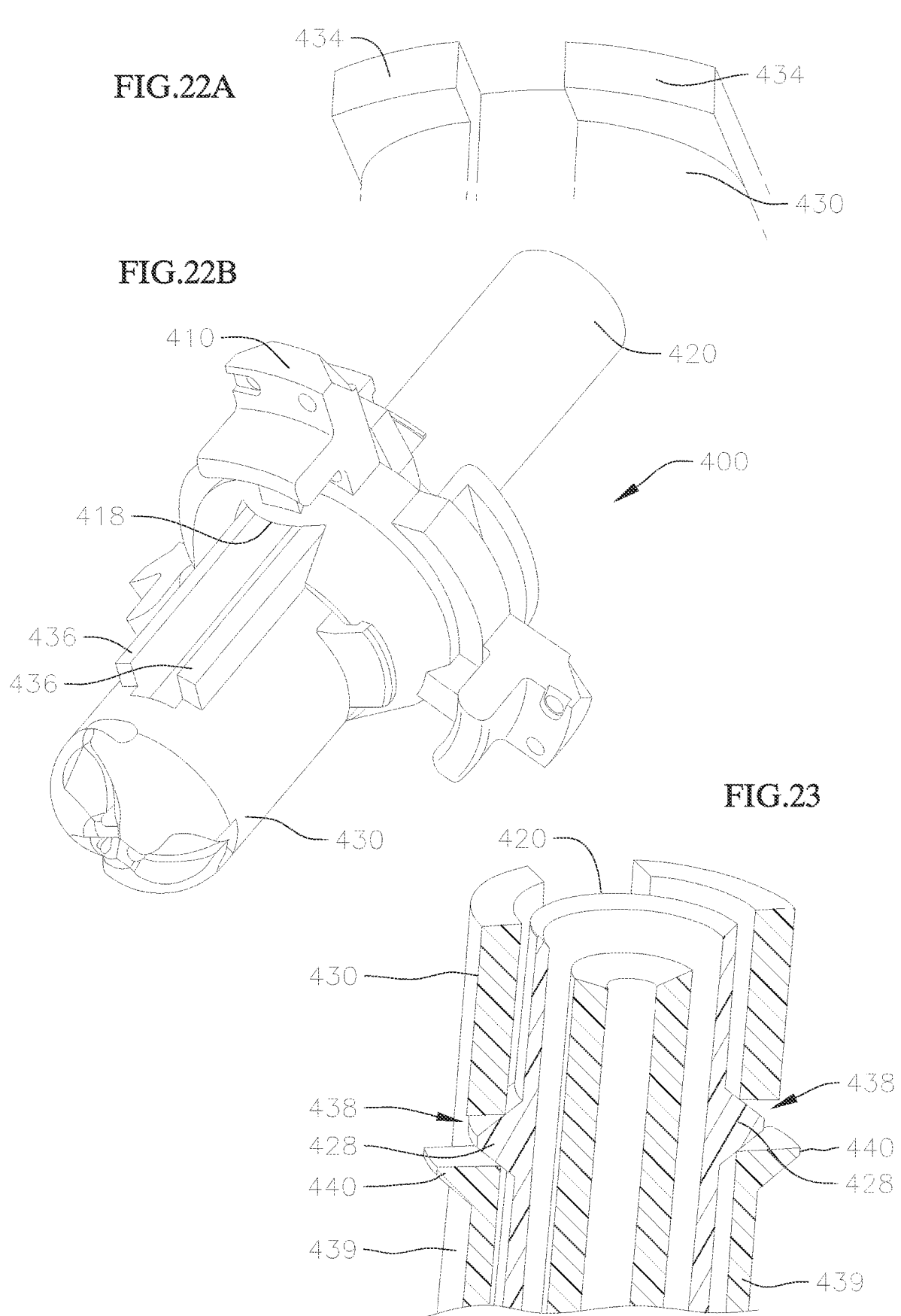
FIG. 22A shows an enlarged perspective view of a portion of a modified post of the valve holder of FIG. 18.
FIG. 22B shows a perspective view of the valve holder with another view of a modified post.
FIG. 23 shows a cross-sectional view of a portion of another modified version of the valve holder of FIG. 18.

FIGS. 22A and 22B schematically show features that can be added to the post and/or the hub of the modified valve holder of FIG. 18, to prevent the post from falling out of the distal end of the hub. FIG. 22A is an enlarged perspective view showing a proximal end of the post 430, where one or more flanges 434 is added to the proximal end of the post 430. The flanges 434 can be formed as projections that extend radially outwardly from other portions of the post 430, and can for example, be integrally molded when the post 430 is formed, or can for example, be attached to the post 430 by ultrasonic welding. A surface of the flanges 434 facing away from the proximal end of the post 430 can provide an abutment against distal movement of the post 430 at certain positions relative to the hub 410. For example, the flanges 434 can abut against a complementary abutting surface (not shown) on the hub 410 when the valve holder 400 is in the deployed position, so that when the prosthetic valve is detached from the valve holder, the flanges 434 on post 430 and corresponding surfaces on the hub 410 prevent the post 430 from detaching distally from the hub 410.

FIG. 22B shows a perspective view of the modified valve holder of FIG. 18 with another modified feature of post 430. In various different embodiments, the modifications shown in FIG. 22B can be incorporated into the valve holder 400 in addition to, or in lieu of, flanges 434 on post 430 shown in FIG. 22A. In the valve holder 400 shown in FIG. 22B, the hub 410 and post 430 are configured such that the post 430 can be loaded or attached to the hub 410 from the proximal or inflow side (e.g., before attachment of the adapter 420 to the hub 410). To facilitate proximal loading of the post 430, the hub 410 can be modified so that the longitudinally extending supports 412 in the inner cavity 411 of hub 410 are removed, and instead, one or more longitudinal alignment grooves 418 can be formed in their place, where the grooves 418 would not impede or block movement of the post 430 through the inner cavity 411. Meanwhile, one or more longitudinally extending tongues 436 can be formed on an outer surface of the post 430 to extend into the grooves 418 when the post 430 is assembled to the hub 410, where the tongues 436 and grooves 418 guide movement between the hub 410 and the post 430.

In addition to the above modifications, one or more stops can then also be added to the post 430 to limit the distal advancement of the post 430 relative to the hub 410. For example, flanges 434 similar to those described with respect to FIG. 22A above can be incorporated into the post 430 to prevent further distal movement or falling out of the post 430 when the valve holder 400 is in the deployed configuration, or other flanges can instead be added to other parts of the post 430. Having projections or protrusions on the post 430 may impede or block loading of the post 430 in designs where the post 430 is assembled from the distal end of the hub 410. However, modifying the valve holder 400 as shown in FIG. 22B, so that the post 430 can be loaded proximally into the hub 410, allows for more flexibility in providing flanges or other outwardly extending features on the post 430 to limit the proximal motion of the post 430, since such features will not impede the assembly of the post 430 through the hub 410.

The additional features discussed above, such as the groove 418, the flanges 434, the tongues 436, or any other stops, projections, or grooves that are formed on either the hub 410 or the post 430, can be easily integrally formed on or in its respective component. For example, each of the features discussed above can be injection molded when the respective components themselves are formed, so that additional processes such as welding or other bonding of parts may not be needed to form the modified components. In other embodiments, however, it may still be desirable or easier to first manufacture parts of one or more of the components separately, and then to weld or otherwise attach the parts of the component or components together thereafter.

FIG. 23 shows a cross-sectional view of a portion of another modified version of the valve holder of FIG. 18. The valve holder of FIG. 23 has modified latching features for holding the vale holder in the undeployed position. In FIG. 23, the first latching features 428 of the valve holder are located on the removable tubular adapter 420, and are formed as projections. The projections 428 on the adapter 420 engage grooves 438 that are formed on the tubular portion of post 430. The tubular portion of the post 430 can be formed similarly to the tubular portion of the post 230 described with respect to earlier embodiments, where diametrically opposite longitudinal extensions 439 are formed with second latching features 440 at the free ends thereof. The second latching features 440 can later be used to hold the post 430 at the deployed position relative to the hub 410. Meanwhile, rather than also forming the first latching features at the free ends of the extensions 439, inner surfaces of the free ends of the extensions 439 are flat or cylindrical, and spaces formed between the extensions 439 and the rest of the tubular portion provide the grooves 438 into which the projections 428 on the adapter 420 latch. Here, when the valve holder moves from the undeployed position to the deployed position, the post 430 moves distally relative to the hub 410 and the adapter 420, and the projections 428 disengage from the grooves 438. The projections 428 may then force the free ends of the tubular portion of the post 430 slightly radially outwards, or the adapter 420 itself slightly radially inwards, or both, until the entire post 430 moves distally past the projections 428 and further towards the deployed position.

Embodiments of the valve holder can be modified as seen in FIG. 23, or in various other ways, to provide more manufacturing friendly designs. For example, the ends of the extensions 439 on the post 430 in FIG. 23 are easier to manufacture, because the inner radius of the entire tubular portion of the post 430 can be manufactured to have a generally uniform cylindrical shape, without the need to maintain or form any inwardly extending projections, while additional grooves on the adapter 420, to accommodate any such inwardly extending projections would also no longer be necessary.

In other alternative embodiments, various different features from the different embodiments discussed above can also be combined into a single modified valve holder. In addition, various other modifications or alternative configurations can also be made to the valve holder according to the above described embodiments of the invention.

For purposes of this description, certain aspects, advantages, and novel features of the embodiments of this disclosure are described herein. The disclosed methods, apparatus, and systems should not be construed as being limiting in anyway. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art.

In view of the many possible embodiments to which the principles of the disclosure can be applied, it should be recognized that the illustrated embodiments are only preferred examples and should not be taken as limiting the scope of the disclosure. Rather, the scope of the disclosure is defined by the following claims.

What is claimed is:

1. A system for delivering a prosthetic heart valve, the heart valve defining an inflow end and comprising a valve stent with and a plurality of commissure posts projecting in an outflow direction and a plurality of flexible leaflets connected to the commissure posts and arranged to coapt along a flow axis, the system having a valve holder comprising:

a hub body having a distal end, a proximal end, and a throughbore along a central axis extending between the distal and proximal ends, the hub body being adapted to abut the inflow end of the heart valve such that the throughbore is aligned with the flow axis;

a hub adapter connected to the proximal end of the hub body to form a hub assembly, the hub adapter having a tubular portion defining a coaxial bore comprising a distal region having an engagement portion and a proximal portion, the bore being aligned with the hub body throughbore;

a post movable relative to the hub assembly so that a distal end of the post extends past an outflow end of the valve when the valve holder is attached to the inflow end of the valve, the post comprising a longitudinally extending central body configured to be positioned within the aligned bore and throughbore and a tubular section coaxial with and spaced around the central body, the tubular section being sized to pass through the throughbore while extending around the tubular portion of the hub adapter; and a plurality of sutures connected to and extending distally from the distal end of the hub body to engage respective commissure posts of the heart valve, wherein the sutures form a crossing region on the flow axis at a first distance from the distal end of the hub body;

the system further including, a delivery handle for advancing the valve holder and the heart valve to the implant site, the delivery handle having a distal end configured to engage the engagement portion at the distal region of the bore of the hub adapter and adjust the valve holder to a deployed configuration from an un-deployed configuration;

wherein in the un-deployed configuration of the valve holder, the distal end of the post is at a first position that is spaced apart from the crossing region, and wherein in the deployed configuration, the post has moved distally and the distal end of the post is at a second position in contact with the crossing region so as to distally displace the crossing region and inwardly deflect commissure posts of the heart valve, and the hub adapter may be detached from the hub body while the distal end of the post remains in the second position.

2. The system of claim 1, wherein the hub body comprises three radially extending projections on which the sutures are configured to be attached.

3. The system of claim 1, wherein at least one of the hub body or the post comprises a latch for holding the valve holder in at least one of the un-deployed configuration or the deployed configuration.

4. The system of claim 1, wherein the engagement portion in the distal region of the bore is threaded and the distal end of the delivery handle is threaded so as to mate thereto, and the proximal region of the bore is larger than the distal region and unthreaded so as to align the delivery handle with the threaded engagement portion.

5. The system of claim 1, wherein the distal end of the post has at least one groove configured to engage the crossing region of the sutures.

6. The system of claim 5, wherein the distal end of the post has an axially extending hole for engagement with a pin during attachment of the heart valve.

7. The system of claim 1, further comprising one or more axial projections configured to guide relative movement between the post and the bore.

8. The system of claim 1, wherein the hub adapter and hub body are connected by one or more sutures.

9. The system of claim 8, the hub adapter and hub body are connected by a single suture on one side extending over a single cutting recess to enable detachment of the hub adapter from the hub body, and the hub adapter and hub body together define an interlock portion on a side opposite the cutting recess that combines with the single suture to connect the hub adapter and hub body.

10. The system of claim 9, wherein the interlock portion comprises a radial projection on the hub adapter that fits within an opening in the hub body such that cutting the single suture allows the hub adapter to pivot away from the hub body on the side of the single suture until the radial projection can be pulled from within the opening.

11. A system for delivering a prosthetic heart valve, the heart valve defining an inflow end and comprising a valve stent with and a plurality of commissure posts projecting in an outflow direction and a plurality of flexible leaflets connected to the commissure posts and arranged to coapt along a flow axis, the system comprising:

a valve holder comprising a hub assembly of a hub body connected to a hub adapter, the hub body configured to abut the inflow end of the heart valve, and the hub adapter having a coaxial bore extending therethrough opening to a proximal end of the valve holder and to an aligned throughbore in the hub body, wherein a distal region of the bore has female threading;

a post positioned in the bore and movable though the bore and throughbore in the hub assembly so that a distal end of the post extends past an outflow end of the valve when the valve holder is attached to the inflow end of the valve; and a plurality of sutures connected to the hub body and engage respective commissure posts of the heart valve, wherein the sutures form a crossing region on the flow axis at a first distance from the distal end of the hub body; and a delivery handle for advancing the valve holder and the heart valve to the implant site, the delivery handle comprising a male threaded distal end configured to engage the female threading at the distal region of the bore of the hub adapter;

wherein when the male threaded distal end of the delivery handle advances along the female threading of the bore, the delivery handle adjusts the valve holder to a deployed configuration from an un-deployed configuration by distally moving the post to a deployed position into contact with and distally displace the crossing region of the sutures and inwardly deflect commissure posts of the heart valve, and wherein in the deployed position the post is configured to engage the hub body to prevent proximal movement, and the hub adapter with the delivery handle may be detached from the hub body while the valve holder remains in the deployed configuration.

12. The system of claim 11, wherein the hub body comprises three radially extending projections on which the sutures are configured to be attached.

13. The system of claim 11, wherein at least one of the hub body or the post comprises a latch for holding the valve holder in at least one of the un-deployed configuration or the deployed configuration.

14. The system of claim 11, wherein the proximal region of the bore is larger than the distal region and unthreaded so as to align the male threaded distal end of the delivery handle with the female threading of the bore.

15. The system of claim 11, wherein the distal end of the post has at least one groove configured to engage the crossing region of the sutures.

16. The system of claim 11, further comprising one or more axial projections configured to guide relative movement between the post and the bore.

17. The system of claim 11, the hub adapter and hub body are connected by a single suture on one side extending over a single cutting recess to enable detachment of the hub adapter from the hub body, and the hub adapter and hub body together define an interlock portion on a side opposite the cutting recess that combines with the single suture to connect the hub adapter and hub body.

18. The system of claim 17, wherein the interlock portion comprises a radial projection on the hub adapter that fits within an opening in the hub body such that cutting the single suture allows the hub adapter to pivot away from the hub body on the side of the single suture until the radial projection can be pulled from within the opening.

19. The system of claim 11, wherein when the valve holder has been adjusted to the deployed configuration by the delivery handle, the valve holder remains in the deployed configuration by a latch on the post that engages a ledge on the hub body.

20. The system of claim 11, wherein at least one of the hub adapter or the post comprises an abutment for restricting movement of the post in a direction toward the proximal end of the hub when the valve holder is in the un-deployed configuration.

* * * * *